(12) United States Patent
Kawano et al.

(10) Patent No.: US 8,129,163 B2
(45) Date of Patent: Mar. 6, 2012

(54) GENE SUITABLE FOR ALCOHOL DEHYDROGENASE, VECTOR AND TRANSFORMANT

(75) Inventors: Shigeru Kawano, Takasago (JP); Takeru Ishige, Takasago (JP); Keita Iguchi, Takasago (JP); Tozo Nishiyama, Takasago (JP); Yoshihiko Yasohara, Takasago (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 116 days.

(21) Appl. No.: 12/516,388

(22) PCT Filed: Nov. 27, 2007

(86) PCT No.: PCT/JP2007/072813
§ 371 (c)(1),
(2), (4) Date: Aug. 27, 2009

(87) PCT Pub. No.: WO2008/066018
PCT Pub. Date: Jun. 5, 2008

(65) Prior Publication Data
US 2010/0035317 A1 Feb. 11, 2010

(30) Foreign Application Priority Data
Nov. 29, 2006 (JP) .................................. 2006-321139

(51) Int. Cl.
C12N 9/00 (2006.01)
C12N 9/02 (2006.01)
C12N 1/20 (2006.01)
C12N 15/00 (2006.01)
C07H 21/04 (2006.01)

(52) U.S. Cl. ..................... 435/189; 435/183; 435/252.3; 435/320.1; 536/23.2

(58) Field of Classification Search .................. None
See application file for complete search history.

(56) References Cited

U.S. PATENT DOCUMENTS

| 5,334,507 A | 8/1994 | Soya et al. |
| 5,763,236 A | 6/1998 | Kojima et al. |

FOREIGN PATENT DOCUMENTS

| EP | 533183 A2 | 3/1993 |
| EP | 645453 A2 | 3/1995 |
| JP | 5-103697 A | 4/1993 |
| JP | 7-231785 A | 9/1995 |
| JP | 2003-169696 A | 6/2003 |
| JP | 3574682 | 10/2004 |
| JP | 2005-102511 A | 4/2005 |
| JP | 2005-533497 | 11/2005 |
| WO | WO-2004/009807 A1 | 1/2004 |

OTHER PUBLICATIONS

Accession O42703. Published Jun. 1, 1998.*
Chica et al. Curr Opin Biotechnol. Aug. 2005;16(4):378-84.*
Sen et al. Appl Biochem Biotechnol. Dec. 2007;143(3):212-23.*
Accession AB010636. Publsiehd Jan. 28, 1998.*
UNIPROT: Q5A958 (XP002561805), Apr. 26, 2005.
GENESEQP: AAY95047 (XP002561806), Jun. 23, 2000.
JPOP: BD675875 (XP002561807), Nov. 19, 2003.

* cited by examiner

Primary Examiner — Christian Fronda
(74) Attorney, Agent, or Firm — Connolly Bove Lodge & Hutz LLP

(57) ABSTRACT

An object of the present invention is to provide a novel alcohol dehydrogenase, a gene for the alcohol dehydrogenase, a vector including the gene, a transformant transformed with the vector, and a method for producing an optically active alcohol by utilizing them. A feature of the present invention directs to a novel polypeptide isolated from *Candida maltosa*, a DNA coding for the polypeptide, and a transformant producing the polypeptide. Another feature of the present invention directs to a method for producing an optically-active alcohol by reducing a carbonyl compound with the polypeptide or the transformant.

13 Claims, 1 Drawing Sheet

SEQUENCE LISTING

<160> NUMBER OF SEQ ID NOS: 13

<210> SEQ ID NO 1
<211> LENGTH: 336
<212> TYPE: PRT
<213> ORGANISM: Candida maltosa

<400> SEQUENCE: 1

Met Ser Ile Pro Ser Thr Gln Tyr Gly Phe Tyr Tyr Thr Lys Glu Lys
1               5                   10                  15

Gly Leu Thr Leu Lys Gln Asp Leu Pro Val Pro Lys Pro Ala Ala Gly
            20                  25                  30

Gln Leu Leu Met Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Leu Gly Ala Glu Val Asp Gly
65                  70                  75                  80

Phe Ala Val Gly Asp Arg Val Ala Cys Val Gly Pro Asn Gly Cys Gly
                85                  90                  95

Ile Cys Lys His Cys Leu Lys Gly Glu Asp Asn Val Cys Lys Lys Ala
            100                 105                 110

Phe Gly Asp Trp Phe Gly Leu Gly Ser Asp Gly Gly Tyr Glu Glu Tyr
        115                 120                 125

Leu Leu Val Arg Arg Pro Arg Asn Leu Val Lys Ile Pro Asp Asn Val
    130                 135                 140

Thr Thr Glu Glu Ala Ala Ala Ile Thr Asp Ala Val Leu Thr Pro Tyr
145                 150                 155                 160

His Ala Ile Lys Val Ala Gly Val Gly Pro Thr Thr Asn Leu Leu Ile
                165                 170                 175

Val Gly Ala Gly Gly Leu Gly Gly Asn Ala Ile Gln Val Ala Lys Ala
            180                 185                 190

Phe Gly Ala Thr Val Thr Val Leu Asp Lys Lys Asp Lys Ala Arg Glu
        195                 200                 205

Gln Ala Lys Ser Leu Gly Ala Asp Asn Val Tyr Asp Glu Leu Pro Ser

```
                    210                 215                 220
Ser Val Glu Pro Gly Ser Phe Asp Val Cys Ile Asp Phe Val Ser Val
225                 230                 235                 240

Gln Ala Thr Phe Asp Leu Cys Gln Thr Tyr Cys Glu Pro Lys Gly Thr
                245                 250                 255

Ile Ile Pro Val Gly Leu Gly Ala Ser Asn Leu Ser Ile Asn Leu Gly
                260                 265                 270

Asp Leu Asp Leu Arg Glu Ile Arg Val Leu Gly Ser Phe Trp Gly Thr
            275                 280                 285

Ser Leu Asp Leu Arg Glu Ala Phe Glu Leu Ala Ala Gln Gly Lys Val
290                 295                 300

Lys Pro Val Val Ala His Ala Glu Leu Lys Glu Leu Pro Glu Tyr Ile
305                 310                 315                 320

Glu Lys Leu Lys Lys Gly Ala Tyr Glu Gly Arg Val Val Phe His Pro
                325                 330                 335
```

<210> SEQ ID NO 2
<211> LENGTH: 1011
<212> TYPE: DNA
<213> ORGANISM: Candida maltosa

<400> SEQUENCE: 2

```
atgtcaattc catctactca atacggtttc tattacacta agaaaaaagg tttaaccttg      60
aaacaagatt tacctgttcc taaaccagct gctggtcaat gttgatgaa ggtcgatgcc     120
gttggtttat gtcactctga tttacatgtc atttatgaag ggttagattg tggggataac     180
tatgtcatgg gacatgaaat tgccggtact gttgctgctt tgggtgctga agttgacggt     240
tttgctgttg gtgatcgtgt tgcttgtgtt ggtccaaatg gttgtggtat ctgtaaacat     300
tgttttgaaag gtgaagataa cgtttgtaag aaggcttttg gtgattggtt tggtttaggt     360
agtgatggtg ttatgaaga atacttgttg gttagaagac aagaaatttt ggttaaaatc     420
ccagataatg tcactactga gaagctgcc gctattactg atgctgtttt gactccttac     480
catgctatta aggttgctgg tgttggtcca actactaatc ttttaattgt tggtgctggt     540
ggtttgggtg gtaatgctat ccaagttgcc aaagcttttg gtgctacagt tactgttttg     600
gataagaaag ataaggctcg tgaacaagct aagagtttgg gtgctgataa tgtttatgat     660
gaattaccat caagtgtcga accaggttct tttgatgtat gtattgattt tgtgtctgtt     720
caagcaactt ttgaccttg tcaaacatat tgtgaaccaa aggtaccat cattccagtt     780
ggtttaggtg cttcaaatct ttccatcaac cttggtgatt tagatcttcg tgaaatcaga     840
gttttgggta gtttctgggg tacctctttg gacttgagag aagcttttga attggccgct     900
caaggtaaag tcaaaccagt tgttgcccat gctgaattga agaattacc agaatacatt     960
gaaaaattga gaaaggtgc ttatgaaggt agagttgttt tccatccata a              1011
```

<210> SEQ ID NO 3
<211> LENGTH: 20
<212> TYPE: DNA
<213> ORGANISM: Artificial
<220> FEATURE:
<223> OTHER INFORMATION: Primer 1

<400> SEQUENCE: 3

```
ggtgattggt tyggttttrgg                                                   20
```

<210> SEQ ID NO 4
<211> LENGTH: 20

```
<212> TYPE: DNA
<213> ORGANISM: Artificial
<220> FEATURE:
<223> OTHER INFORMATION: Primer 2

<400> SEQUENCE: 4
swagcaccya aaccaactgg                                                 20

<210> SEQ ID NO 5
<211> LENGTH: 416
<212> TYPE: DNA
<213> ORGANISM: Candida maltosa

<400> SEQUENCE: 5
gtagtgatgg tggttatgaa gaatacttgt tggttagaag accaagaaat ttggttaaaa    60
tcccagataa tgtcactact gaagaagctg ccgctattac tgatgctgtt ttgactcctt   120
accatgctat taaggttgct ggtgttggtc caactactaa tcttttaatt gttggtgctg   180
gtggtttggg tggtaatgct atccaagttg ccaaagcttt tggtgctaca gttactgttt   240
tggataagaa agataaggct cgtgaacaag ctaagagttt gggtgctgat aatgtttatg   300
atgaattacc atcaagtgtc gaaccaggtt cttttgatgt atgtattgat tttgtgtctg   360
ttcaagcaac ttttgacctt tgtcaaacat attgtgaacc aaaaggtacc atcatt      416

<210> SEQ ID NO 6
<211> LENGTH: 35
<212> TYPE: DNA
<213> ORGANISM: Artificial
<220> FEATURE:
<223> OTHER INFORMATION: Primer 3

<400> SEQUENCE: 6
gggaattcca tatgtcaatt ccatctactc aatac                                35

<210> SEQ ID NO 7
<211> LENGTH: 33
<212> TYPE: DNA
<213> ORGANISM: Artificial
<220> FEATURE:
<223> OTHER INFORMATION: Primer 4

<400> SEQUENCE: 7
ccggaattct tatggatgga aaacaactct acc                                  33

<210> SEQ ID NO 8
<211> LENGTH: 33
<212> TYPE: DNA
<213> ORGANISM: Artificial
<220> FEATURE:
<223> OTHER INFORMATION: Primer 5

<400> SEQUENCE: 8
ccggaattct aaggaggtta acaatgtata aag                                  33

<210> SEQ ID NO 9
<211> LENGTH: 29
<212> TYPE: DNA
<213> ORGANISM: Artificial
<220> FEATURE:
```

```
<223> OTHER INFORMATION: Primer 6

<400> SEQUENCE: 9
acgcgtcgac ttatccgcgt cctgcttgg                                    29

<210> SEQ ID NO 10
<211> LENGTH: 35
<212> TYPE: DNA
<213> ORGANISM: Artificial
<220> FEATURE:
<223> OTHER INFORMATION: Primer 7

<400> SEQUENCE: 10
accaccgaat tctaaggagg ttaacaatgg cgaaa                             35

<210> SEQ ID NO 11
<211> LENGTH: 31
<212> TYPE: DNA
<213> ORGANISM: Artificial
<220> FEATURE:
<223> OTHER INFORMATION: Primer 8

<400> SEQUENCE: 11
ccaccagagc tctcagccgg ccttcttgaa c                                 31

<210> SEQ ID NO 12
<211> LENGTH: 29
<212> TYPE: DNA
<213> ORGANISM: Artificial
<220> FEATURE:
<223> OTHER INFORMATION: Primer 9

<400> SEQUENCE: 12
tcggcgtcga cgagttcctt ctcgaacac                                    29

<210> SEQ ID NO 13
<211> LENGTH: 29
<212> TYPE: DNA
<213> ORGANISM: Artificial
<220> FEATURE:
<223> OTHER INFORMATION: Primer 10

<400> SEQUENCE: 13
gtgttcgaga aggaactcgt cgacgccga                                    29
```

GENE SUITABLE FOR ALCOHOL DEHYDROGENASE, VECTOR AND TRANSFORMANT

CROSS REFERENCE TO RELATED APPLICATIONS

This application is a National Stage of PCT/JP2007/072813 filed Nov. 27, 2007 which in turn claims priority from Japanese Application 2006-321139 filed Nov. 29, 2006, the entire contents of which are incorporated herein by reference.

FIELD OF THE INVENTION

The present invention relates to a novel alcohol dehydrogenase, a gene for the alcohol dehydrogenase, a vector including the gene, a transformant transformed with the vector, and a method for producing an optically active alcohol by utilizing them.

BACKGROUND OF THE INVENTION

Alcohol dehydrogenases that react with secondary alcohol compounds, such as 2-butanol, are useful enzymes in syntheses of optically active alcohol compounds through stereoselective reduction reaction of carbonyl compounds or syntheses of optically active secondary alcohol compounds through stereoselective oxidation reaction of racemates of secondary alcohols.

Among alcohol dehydrogenases yielded by microorganisms, there are many reports on alcohol dehydrogenases that require nicotinamide adenine dinucleotide (hereafter to be abbreviated as "$NAD^+$") as a coenzyme, and oxidize 2-butanol. There are, however, few reports on alcohol dehydrogenases that preferentially oxidize (S)-2-butanol in comparison with (R)-2-butanol and whose corresponding structural gene (a DNA coding for an enzyme) has been acquired.

As such an alcohol dehydrogenase, enzymes derived from *Gordonia* sp. strain TY-5, and *Candida parapsilosis* IFO 1396 strain have been known.

Among the above enzymes, ADH1, which is an enzyme derived from *Gordonia* sp. strain TY-5, is characterized in that it has a molecular weight of approximately 35,000 as determined by SDS-polyacrylamide electrophoresis, and has an optimum temperature of 30° C. and an optimum pH of 10 in oxidation of 2-propanol. ADH3, which is an enzyme derived from the same strain, is characterized in that it has a molecular weight of approximately 58,000 as determined by SDS-polyacrylamide electrophoresis, and has an optimum temperature of 60° C. and an optimum pH of 10 in oxidation of 2-propanol (See the Patent Document 1 listed below).

An enzyme derived from *Candida parapsilosis* IFO 1396 strain is characterized in that it has a molecular weight of approximately 40,000 as determined by SDS-polyacrylamide electrophoresis, a stable pH range of 8.0 to 10.0, and an appropriate temperature range for action in oxidation of (S)-2-butanol is 25° C. to 55° C. This enzyme has a character that activity of the enzyme is inhibited by 2-mercaptoethanol or dithiothreitol, whereas it is not inhibited by ethylenediaminetetraacetic acid (See the Patent Document 2 listed below).

Thus, there are few alcohol dehydrogenases that preferentially oxidize (S)-2-butanol in comparison with (R)-2-butanol and whose corresponding structural gene (a DNA coding for an enzyme) has been acquired. In view of the state of the art, acquisition of novel enzymes or their corresponding structural gene has been desired. If the structural gene of such enzymes is acquired, the enzyme can be produced through a genetic engineering technique in a large amount, and thereby enables to establish a process that can produce useful compounds, for example, optically active alcohols, with the enzyme in a remarkably efficient manner.

Patent Document 1:JP-A-2005-102511
Patent Document 2:JP-B-3574682

DISCLOSURE OF THE INVENTION

Problem which the Invention is to Solve

It is an object of the present invention to provide a novel alcohol dehydrogenase, a gene for the alcohol dehydrogenase, a vector including the gene, a transformant transformed with the vector, and a method for producing an optically active alcohol by utilizing them.

Means for Solving the Problem

The present invention has one or a plurality of the following technical feature(s):

One of the features of the present invention is a polypeptide having the following physicochemical properties:
(1) Action:
    The polypeptide oxidizes an alcohol with $NAD^+$ as a coenzyme to produce a ketone or an aldehyde. Furthermore, the polypeptide reduces a ketone or an aldehyde with NADH as a coenzyme to produce an alcohol.
(2) Substrate Specificity:
    A substrate in oxidation reaction is an aliphatic alcohol which may have an aromatic substituent. The polypeptide preferentially oxidizes (S)-2-butanol in comparison with (R)-2-butanol; a substrate in reduction reaction is a ketone or an aldehyde. The polypeptide reacts with acetophenone to reduce into (S)-1-phenylethanol.
(3) Molecular Weight:
    The molecular weight of the polypeptide is approximately 39,000 as determined by reducing SDS-polyacrylamide electrophoresis.
(4) Stability in pH:
    Stable pH range of the polypeptide is 5.5 to 7.5.
(5) Optimum Temperature:
    Optimum temperature of the polypeptide for oxidation reaction of (S)-2-butanol is 45° C. to 70° C.
(6) Inhibitor:
    Enzyme activity of the polypeptide is inhibited by ethylenediaminetetraacetic acid, o-phenanthroline, mercury chloride, copper sulfate or zinc sulfate, whereas it is not inhibited by 2-mercaptoethanol or dithiothreitol.

Another feature of the present invention is a polypeptide which is any one of the following polypeptides (a), (b), and (c):
(a) A polypeptide including the amino acid sequence shown under SEQ ID NO:1 in the sequence listing;
(b) A polypeptide including an amino acid sequence that results from deletion, insertion, substitution and/or addition of one amino acid residue or a plurality of amino acid residues in the amino acid sequence shown under SEQ ID NO:1 in the sequence listing, and having activity to react with acetophenone to reduce into (S)-1-phenylethanol; and
(c) A polypeptide having sequence identity of 85% or higher to the amino acid sequence shown under SEQ ID NO:1 in the sequence listing, and having activity to react with acetophenone to reduce into (S)-1-phenylethanol.

Still another feature of the present invention is a DNA coding for the above polypeptide.

Still another features of the present invention are a DNA which is either one of the following DNAs (A) and (B), a vector including this DNA, and a transformant produced by transformation of a host cell with this vector.

(A) a DNA including the base sequence shown under SEQ ID NO:2 in the sequence listing;
(B) a DNA hybridizable under a stringent condition with a DNA that includes the base sequence complementary to the base sequence shown under SEQ ID NO:2 in the sequence listing, and coding for a polypeptide that has activity to react with acetophenone to reduce into (S)-1-phenylethanol;
(C) a DNA having sequence identity of 85% or higher to the base sequence shown under SEQ ID NO:2 in the sequence listing, and coding for a polypeptide that has activity to react with acetophenone to reduce into (S)-1-phenylethanol; and
(D) a DNA including a base sequence that results from deletion, insertion, substitution and/or addition of one base or a plurality of bases in the base sequence shown under SEQ ID NO:2 in the sequence listing, and coding for a polypeptide that has activity to react with acetophenone to reduce into (S)-1-phenylethanol.

Still another feature of the present invention is a method for producing an alcohol, particularly an optically-active alcohol, the method including reacting the polypeptide of the present invention, or the transformant of the present invention, in which the DNA is introduced, and a processed product of the transformant with a carbonyl group-containing compound.

Effect of the Invention

The present invention provides a novel alcohol dehydrogenase, a gene for the alcohol dehydrogenase, a vector including the gene, a transformant transformed with the vector, and a method for producing an optically active alcohol produced by utilizing any of these.

BRIEF DESCRIPTION OF THE DRAWINGS

FIG. 1 illustrates a method for constructing recombinant vectors pNCM, pNCMG and pNCMFT, and structures of them.

BEST MODE FOR CARRYING OUT THE INVENTION

Figure 1:
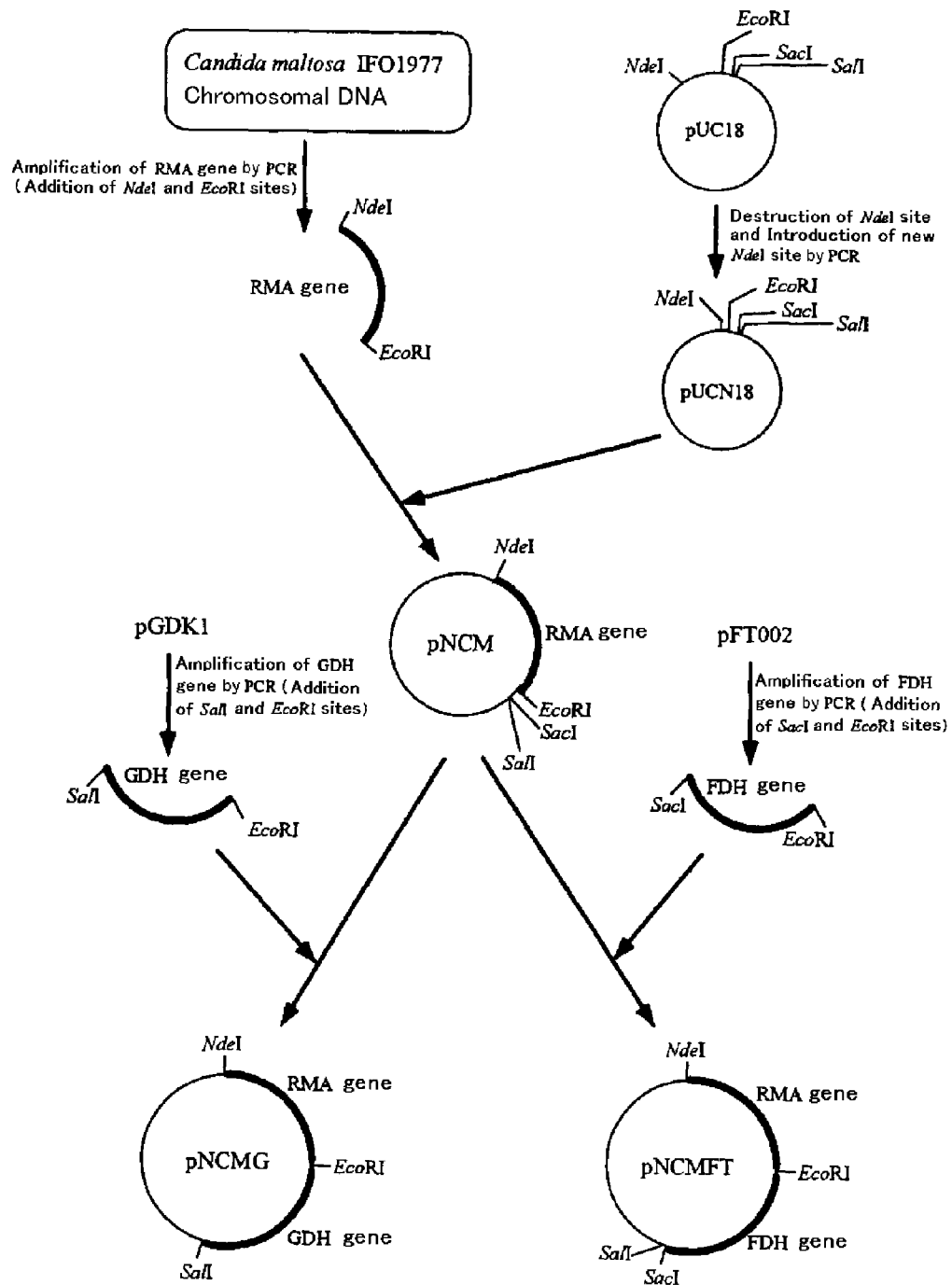
[FIG. 1]

The present invention will be described below in detail with reference to specific embodiments. The present invention is, however, not limited to the following embodiments.
Regarding Various Physical Properties of the Polypeptide of the Present Invention In the present invention, the polypeptide, which is isolated by a method mentioned below, has the following physicochemical properties (1) to (6):
(1) Action:
The polypeptide oxidizes an alcohol with $NAD^+$ as a coenzyme to produce a ketone or an aldehyde. Furthermore, the polypeptide reduces a ketone or an aldehyde with NADH as a coenzyme to produce an alcohol.
(2) Substrate Specificity:
A substrate in oxidation reaction is an aliphatic alcohol which may have an aromatic substituent. The polypeptide preferentially oxidizes (S)-2-butanol in comparison with (R)-2-butanol. A substrate in reduction reaction is a ketone or an aldehyde. The polypeptide reacts with acetophenone to reduce into (S)-1-phenylethanol.
(3) Molecular Weight:
The molecular weight of the polypeptide is approximately 39,000 as determined by reducing SDS-polyacrylamide electrophoresis.
(4) Stability in pH:
Stable pH range of the polypeptide is 5.5 to 7.5.
(5) Optimum Temperature:
Optimum temperature of the polypeptide for action is 45° C. to 70° C.
(6) Inhibitor:
Enzyme activity of the polypeptide is inhibited by ethylenediaminetetraacetic acid, o-phenanthroline, mercury chloride, copper sulfate or zinc sulfate.

The above physicochemical properties (1) to (6) are explained in the followings.
Regarding (1) Action
The polypeptide of the present invention has ability to oxidize, under the presence of $NAD^+$, a secondary alcohol compound to covert into a ketone compound. Furthermore, the polypeptide of the present invention has ability to oxidize an primary alcohol compound to convert into an aldehyde compound.

The ability to oxidize an alcohol compound may be evaluated in the following manner, for example.
[Method for Evaluating Oxidizing Ability to an Alcohol Compound]
Progress of oxidization reaction may be easily evaluated by, at first, preparing a reaction mixture including 2.5 $mMNAD^+$, a 50 mM target alcohol compound, oxidation activity of which is to be evaluated, and a polypeptide of the present invention in 50 mM tris-HCl buffer (pH 9.0), then allowing the reaction mixture to react at 30° C. and finally observing increase of absorbance at the wavelength of 340 nm, which is accompanied by increase of NADH level. If the absorbance is increased, the polypeptide of the present invention has ability to oxidize a target alcohol compound. Rapid increasing rate of the absorbance reflects high ability of the polypeptide of the present invention to oxidize a target alcohol compound. The oxidizing ability of a polypeptide may be expressed in terms of numerical values. Thus, oxidizing activity 1 U is defined as an enzyme level that catalyzes generation of 1 μmol of NADH per minute.

In addition, the polypeptide of the present invention has another ability to reduce a ketone or aldehyde compound into an alcohol compound in the presence of NADH.

The ability to reduce a ketone or aldehyde compound may be evaluated in the following manner, for example.
[Method for Evaluating Reducing Ability to a Ketone or Aldehyde Compound]
Progress of reduction reaction may be easily evaluated by, at first, preparing a reaction solution including 0.25 mM NADH, a 50 mM ketone or aldehyde compound, reduction activity of which is to be evaluated, and a polypeptide of the present invention in 100 mM potassium phosphate buffer (pH 6.5) that contains 0.3% (v/v) of dimethyl sulfoxide, and then allowing the reaction solution to react at 30° C. with monitoring decrease of absorbance at the wavelength of 340 nm, which is accompanied by decrease of NADH level. If the absorbance is decreased, the polypeptide of the present invention has ability to reduce a target ketone or aldehyde compound. Rapid decrease of the absorbance reflects high ability of the polypeptide of the present invention to reduce a target ketone or aldehyde compound. The reducing ability of a polypeptide may be expressed in terms of numerical values.

Thus, reduction activity 1 U is defined as an enzyme level that catalyzes consumption of 1 μmol of NADH per minute.

(2) Regarding Substrate Specificity

A substrate in oxidation reaction is an aliphatic alcohol which may have an aromatic substituent. The substrate specificity may be evaluated in accordance with the [Method for evaluating oxidizing ability to an alcohol compound], as described in the above (1) Action.

The polypeptide of the present invention preferentially oxidizes (S)-2-butanol in comparison with (R)-2-butanol. This preference means that ability to oxidize (S)-2-butanol is higher than that to oxidize (R)-2-butanol. The fact that the ability to oxidize (S)-2-butanol is higher than that to oxidize (R)-2-butanol may be easily confirmed by evaluating oxidizing ability to each of (R)-2-butanol and (S)-2-butanol in accordance with the [Method for evaluating oxidizing ability to an alcohol compound], as described in the above (1) Action.

Furthermore, the polypeptide of the present invention reacts with a ketone and aldehyde substrate in reduction reaction. The substrate specificity may be evaluated in accordance with the [Method for evaluating reducing ability to a ketone or aldehyde compound], as described in the above (1) Action.

The polypeptide of the present invention has ability to react with acetophenone to reduce into (S)-1-phenylethanol. The reducing ability may be tested in the following manner, for example.

In a 100 mM phosphate buffer (pH 7), acetophenone, NADH and the polypeptide of the present invention are added, and then the mixture is allowed to react at 30° C. while stirring. After completion of the reaction, the reaction mixture is extracted with an organic solvent such as ethyl acetate. The extract was analyzed by gas chromatography under the following conditions. Thereby, generation of 1-phenylethanol, configuration thereof, and optical purity thereof may be determined.

[Analysis condition (1) for gas chromatography]
Column: CHIRALDEX G-PN (30 m, 0.25 mm ID) (a product of RESTEK),
Column temperature: 100° C.
Injection temperature: 150° C.
Detection temperature: 150° C.
Detector: FID
Carrier gas: He, 130 kPa
Elution time: acetophenone (9.2 min.)
(S)-1-phenylethanol (14.5 min.)
(R)-1-phenylethanol (15.2 min.)

Regarding (3) Molecular Weight

The molecular weight of the polypeptide of the present invention is approximately 39,000 as determined by reducing SDS-polyacrylamide electrophoresis. The molecular weight may be determined by reducing SDS-polyacrylamide electrophoresis in accordance with a known method, for example, a method taught in a textbook "Seibutsu-kagaku Jikken no Tebiki 2, Tanpakushitsu no Bunri-Bunseki hou" (Guide for Biochemical experiments vol. 2, Method for isolating or separating proteins) (published by Kagaku-dojin Publishing Company, Inc., Tokyo, Japan). The molecular weight of the polypeptide may be calculated from the difference between the polypeptide and a molecular weight standard protein in their mobility.

Regarding (4) Stability in pH

Stable pH range of the polypeptide of the present invention is 5.5 to 7.5. The stable pH range may be determined in the following manner, for example. A polypeptide was treated in some Britton-Robinson buffers, each pH of which is varied, at 30° C. for 30 minutes. Then, the oxidizing ability to (S)-2-butanol is determined in accordance with the [Method for evaluating oxidizing ability to an alcohol compound] as mentioned above. Stable pH range is defined as a pH range where remained activity after the treatment is 80% or higher of the activity of the untreated polypeptide.

Regarding (5) Optimum Temperature:

The polypeptide of the present invention has an optimum temperature for action of enzyme activity of 45° C. to 70° C. The optimum temperature for action may be measured by the following manner, for example. In the above [Method for evaluating oxidizing ability to an alcohol compound], oxidizing activities to (S)-2-butanol are determined at some different temperatures. The oxidizing activity at the temperature that shows the highest activity is defined as 100%. Activity at each temperature is expressed as relative activity to the highest activity. Then, optimum temperature for action is defined as a temperature range that shows 60% or higher relative activity.

Regarding (6) Inhibitors

Enzyme activity of the polypeptide of the present invention is inhibited by ethylenediaminetetraacetic acid, o-phenanthroline, mercury chloride, copper sulfate or zinc sulfate, whereas it is not inhibited by 2-mercaptoethanol or dithiothreitol. Whether or not a compound inhibits enzyme activity of the polypeptide may be evaluated in the following manner, for example. In 1 mM concentration solution or mixture of various compounds, a polypeptide is treated at 30° C. for 30 minutes. Then, oxidizing activity to (S)-2-butanol is determined in accordance with the above-mentioned [Method for evaluating oxidizing ability to an alcohol compound]. When remained activity after the treatment is 30% or lower of enzyme activity of the untreated polypeptide, the compound used in the treatment may be regarded as an inhibitor of the enzyme activity of the polypeptide. On the contrary, when remained activity after the treatment is 90% or higher of enzyme activity of the untreated polypeptide, the compound used in the treatment may not be regarded as an inhibitor of the enzyme activity of the polypeptide.

Regarding Isolation of the Polypeptide of the Present Invention

The polypeptide of the present invention may be selected from polypeptides that has ability to preferentially oxidize (S)-2-butanol in comparison with (R)-2-butanol. Alternatively, the polypeptide of the present invention may be selected from polypeptides that have activity to reduce a carbonyl group-containing compound to produce an alcohol, preferably polypeptides that have activity to asymmetrically reduce asymmetric ketones to produce an optically active alcohol, and the most preferably polypeptides that has activity to asymmetrically reduce acetophenone to produce (S)-1-phenylethanol.

The polypeptides mentioned above may be isolated from organisms such as microorganisms having the above-mentioned activity. The enzyme may be found, for example, in a microorganism according to the following manner. A microorganism in an appropriate medium is cultivated. Cells are collected, and then the cells are reacted with acetophenone in a buffer under the presence of nutriments, such as glucose. After the reaction, the reaction mixture is extracted with a solvent or the like. The resultant extract may be analyzed under a condition described in the above [Analysis condition (1) for gas chromatography], to monitor generation of 1-phenylethanol.

The medium for cultivating microorganisms may be a common liquid nutrient medium which contains carbon sources, nitrogen sources, inorganic salts and organic nutriments, provided that the microorganism can proliferate in the medium. Cultivation may be conducted by shaking the medium or aerating the medium at a temperature within the range of 25° C. to 37° C., and at a pH within the range of 4 to 8.

The polypeptide of the present invention may be isolated from polypeptide source microorganisms by appropriately combining some known methods for purifying proteins. For example, the isolation may be conducted as follows. First, such a microorganism is cultivated in an appropriate medium, and then cells are collected from the culture fluid by centrifugation or filtration. Thus-collected cells are disrupted by a physical process, such as sonication with an ultrasonic disintegrator or milling with glass beads, and then remove residue of the cells by centrifugation. Cell-free extract is thereby obtained. The polypeptide of the present invention is isolated from the cell-free extract by a single or combined technique(s) selected from thermal treatment, salting out (ammonium sulfate precipitation, sodium phosphate precipitation, etc.), solvent precipitation (method for precipitating protein fraction with acetone or ethanol), dialysis, gel filtration chromatography, ion exchange chromatography, reversed phase chromatography, and ultrafiltration.

The polypeptide of the present invention may be derived from any microorganisms and is not particularly limited. Preferable one is a microorganism that belongs to the genus *Candida*. Preferable examples include *Candida maltosa*, and more preferable one may be *Candida maltosa* IFO 1977 strain. *Candida maltosa* IFO 1977 strain is available from the Incorporated Administrative Agency National Institute of Technology and Evaluation, Biotechnology Field, Exploiting the power of Microorganisms for the Development of Bioindustries (NBRC; 2-5-8 Kazusakamatari, Kisarazu-shi, Chiba, 292-0818 JAPAN).

Regarding the Amino Acid Sequence of the Polypeptide of the Present Invention

The polypeptide of the present invention may be any one of the following polypeptide (a), (b), and (c).
(a) A polypeptide including the amino acid sequence shown under SEQ ID NO:1 in the sequence listing;
(b) A polypeptide including an amino acid sequence that results from deletion, insertion, substitution and/or addition of one amino acid residue or a plurality of amino acid residues in the amino acid sequence shown under SEQ ID NO:1 in the sequence listing, and having activity to react with acetophenone to reduce into (S)-1-phenylethanol; and
(c) A polypeptide having sequence identity of 85% or higher to the amino acid sequence shown under SEQ ID NO:1 in the sequence listing, and having activity to react with acetophenone to reduce into (S)-1-phenylethanol.

Three types of polypeptides (a) to (c) are each explained in detail in the followings.

Regarding the Polypeptide (a)

Examples of amino acid sequence of the polypeptide of the present invention include the amino acid sequence shown under SEQ ID NO:1 in the sequence listing, which is encoded by the base sequence shown under SEQ ID NO:2 in the sequence listing.

Regarding the Polypeptide (b)

The polypeptide (b), which includes an amino acid sequence that results from deletion, insertion, substitution and/or addition of one amino acid residue or a plurality of amino acid residues in the amino acid sequence shown under SEQ ID NO:1 in the sequence listing, may be prepared in accordance with a known method such as a method described in Current Protocols in Molecular Biology (John Wiley and Sons, Inc., 1989). The polypeptide (b) encompasses such a polypeptide having activity to react with acetophenone to reduce into (S)-1-phenylethanol.

In the amino acid sequence shown under SEQ ID NO:1 in the sequence listing, sites where amino acids are to be substituted, inserted, deleted, and/or added are not particularly limited, but preferably, highly conserved regions should be avoided. Here, the term "highly conserved region" means a position where, among a plurality of enzymes derived from different sources, amino acids in one sequence coincide with those in other sequences under a condition that amino acid sequences are optimally arranged in line. Highly conserved regions may be determined by comparing, with a tool such as GENETYX, the amino acid sequence shown under SEQ ID NO:1 with an amino acid sequence of alcohol dehydrogenase that derives from a known microorganism.

The amino acid sequence modified by substitution, insertion, deletion and/or addition may include a site modified through one type of modification process (for example, substitution), or may include a site or sites modified through two or more modification process (for example, substitution and insertion).

When the amino acid sequence is modified by substitution, an amino acid for substituting a part of the amino acid sequence is preferably an amino acid having a similar characteristic (homologous amino acids) to the amino acid to be substituted.

In this application, amino acids belonging to the same group as illustrated below are considered as homologous amino acids.
(First group: neutral nonpolar amino acids) Gly, Ala, Val, Leu, Ile, Met, Cys, Pro, Phe
(Second group: neutral polar amino acids) Ser, Thr, Gln, Asn, Trp, Tyr
(Third group: acidic amino acids) Glu, Asp
(Fourth group: basic amino acids) His, Lys, Arg The term "a plurality of amino acid residues" means, for example, 50 or less, preferably 30 or less, more preferably 15 or less, still more preferably 10 or less, 5 or less, 4 or less, 3 or less, or 2 or less amino acids.

Regarding the Polypeptide (c)

The polypeptide of the present invention also includes a polypeptide having sequence identity of 85% or higher to the amino acid sequence shown under SEQ ID NO:1 in the sequence listing, and having activity to react with acetophenone to reduce into (S)-1-phenylethanol. Although a polypeptide having sequence identity of 85% or higher to the amino acid sequence shown under SEQ ID NO:1 in the sequence listing may be within the scope of the polypeptide of the present invention, the sequence identity is preferably 90% or higher, more preferably 95% or higher, still more preferably 98% or higher, and the most preferably 99% or higher.

Sequence identity of an amino acid sequence is expressed as a value determined by, while comparing the amino acid sequence shown under SEQ ID NO:1 in the sequence listing with a target amino acid sequence, dividing the number of positions where amino acids coincide between the two amino acid sequences by the total number of amino acids in the target amino acid sequence, and further multiplying the result by 100.

Additional amino acid sequences may be coupled with the amino acid sequence shown under SEQ ID NO:1 as long as the coupled amino acid sequences have activity to react with acetophenone to reduce into (S)-1-phenylethanol. For example, tag sequences, such as a histidine tag or a HA tag, may be added. The polypeptide of the present invention may be used in a form of fusion protein in combination with another protein. Also, the polypeptide (c) may be a peptide fragment, as long as the fragment has an activity to react with acetophenone to reduce into (S)-1-phenylethanol.

The polypeptide of the present invention also includes a polypeptide having sequence identity of 85% or higher to the amino acid sequence shown under SEQ ID NO:1 in the sequence listing, and having activity to react with acetophenone to reduce into (S)-1-phenylethanol.

Regarding Cloning of DNA Coding for the Polypeptide of the Present Invention

A DNA coding for polypeptide of the present invention may be any DNA that can express the enzyme in a host cell into which the DNA is introduced in a manner described below, and may contain any untranslated region. When the enzyme is obtained, a person skilled in the art would produce such a DNA from an organism that produces the enzyme in a known manner. For example, such a DNA may be obtained in a manner mentioned below.

Gene manipulations such as DNA cloning, construction of a vector, and transformation, which will be described hereafter in this description, may be conducted in accordance with a manner described in literatures such as Molecular Cloning 2nd Edition (Cold Spring Harbor Laboratory Press, 1989) unless otherwise indicated. The "%" used herein means "% (w/v)" unless otherwise specified.

First, a polypeptide of the present invention, which has been isolated by a method described in the "*Regarding isolation of the polypeptide of the present invention*," are digested with an appropriate endopeptidase, and the resultant peptide fragments are batched off with reverse phase HPLC. Then, the amino acid sequence of part of or whole of these peptide fragments are determined with, for example, a type ABI492 protein sequencer (a product of Applied Biosystems).

Based on thus-obtained information about amino acid sequence, PCR (Polymerase Chain Reaction) primers for amplifying a part of a DNA that codes for the polypeptide is synthesized. Then, a chromosomal DNA of a microorganism that produces the polypeptide are prepared in accordance with a common method for isolating DNA, such as a method taught by Visser et al. (Appl. Microbiol. Biotechnol., 53, 415 (2000)). PCR is carried out from these chromosomal DNA templates with the above PCR primers, to amplify a part of the DNA that codes for the polypeptide, and then the base sequence thereof is determined. The base sequence may be determined with, for example, Applied Biosystems 3130xl Genetic Analyzer (a product of Applied Biosystems).

If part of the base sequence of a DNA coding for polypeptide is revealed, the whole sequence may be determined by, for example, Inverse PCR method (Nucl. Acids Res., 16, 8186 (1988).

Examples of the thus-obtained DNA coding for the polypeptide of the present invention include a DNA that includes the base sequence shown under SEQ ID NO:2 in the sequence listing.

The base sequence shown under SEQ ID NO: 2 will be explained below.

Regarding the DNA Coding for the Polypeptide of the Present Invention

Examples of the DNA coding for the polypeptide of the present invention include:

A DNA including the base sequence shown under SEQ ID NO:2 in the sequence listing;

A DNA hybridizable under a stringent condition with a DNA that includes the base sequence complementary to the base sequence shown under SEQ ID NO:2 in the sequence listing, and coding for a polypeptide that has activity to react with acetophenone to reduce into (S)-1-phenylethanol;

A DNA having sequence identity of 85% or higher to the base sequence shown under SEQ ID NO:2 in the sequence listing, and coding for a polypeptide that has activity to react with acetophenone to reduce into (S)-1-phenylethanol; and A DNA including a base sequence that results from deletion, insertion, substitution and/or addition of one base or a plurality of bases in the base sequence shown under SEQ ID NO:2 in the sequence listing, and coding for a polypeptide that has activity to react with acetophenone to reduce into (S)-1-phenylethanol.

Here, the "DNA hybridizable under a stringent condition with a DNA that includes the base sequence complementary to the base sequence shown under SEQ ID NO:2 in the sequence listing, and coding for a polypeptide that has activity to react with acetophenone to reduce into (S)-1-phenylethanol" means a DNA obtainable by colony hybridization technique, plaque hybridization technique, Southern hybridization technique, or the like under a stringent condition with a DNA that includes the base sequence complementary to the base sequence shown under SEQ ID NO:2 in the sequence listing as a probe, and codes for a polypeptide that has activity to react with acetophenone to reduce into (S)-1-phenylethanol.

Hybridization may be conducted, for example, according to a method described in Molecular Cloning, A laboratory manual, second edition (Cold Spring Harbor Laboratory Press, 1989). Here, examples of "a DNA hybridizable under a stringent condition" include DNAs, which are obtainable through hybridization with a filter, onto which a colony- or plaque-derived DNA is immobilized, in the presence of 0.7 to 1.0 M NaCl, at 65° C., followed by washing the filter with a 2-fold concentration of SSC solution (one-fold concentration of the SSC solution consists of 150 mM NaCl and 15 mM sodium citrate) at 65° C. Preferable examples of the DNA include DNAs obtainable by washing with half-fold concentration of the SSC solution at 65° C. More preferable examples thereof include DNAs obtainable by washing with 0.2-fold concentration of the SSC solution at 65° C. Still more preferable examples thereof include DNAs obtainable by washing with 0.1-fold concentration of the SSC solution at 65° C.

Conditions for hybridization are described above, but the condition is not limited to the above described ones. Conceivable factors affecting to stringency in hybridization include a variety of factors, such as temperature conditions, or salt concentrations. A person skilled in the art could attain an optimum stringency by appropriately controlling the above factors.

Examples of such a DNA hybridizable under the above condition include DNAs having sequence identity of 70% or higher, preferably 85% or higher, more preferably 90% or higher, still more preferably 95% or higher, and most preferably 98% or higher to the base sequence shown under SEQ ID NO:2. As long as a polypeptide encoded by a DNA has activity to react with acetophenone to reduce into (S)-1-phenylethanol, the DNA coding for the polypeptide is encompassed within the above DNA.

Here, the "sequence identity (%)" is expressed as a value determined by arranging two DNAs to be compared with one another, dividing the number of positions where nucleobases (for example, A, T, C, G, U, or I) coincide between both sequences by the total number of the bases in the target DNA, and further multiplying the result by 100.

The sequence identity may be calculated by the following sequence analyzers: GCG Wisconsin Package (Program Manual for The Wisconsin Package, Version 8, September 1994, Genetics Computer Group, 575 Science Drive Medison, Wisconsin, USA 53711; Rice, P. (1996) Program Manual for EGCG Package, Peter Rice, The Sanger Centre, Hinxton Hall, Cambridge, CB1O 1RQ, England), and the ExPASy World Wide Web molecular biology server (Geneva University Hospital and University of Geneva, Geneva, Switzerland).

Here, if a DNA having sequence identity of 85% or higher to the base sequence shown under SEQ ID NO:2 in the sequence listing codes for a polypeptide that has activity to react with acetophenone to reduce into (S)-1-phenylethanol, the DNA is encompassed within the range of the DNA of the present invention. Although a DNA having sequence identity of 85% or higher to the base sequence shown under SEQ ID NO:2 in the sequence listing is encompassed within the range of the DNA of the present invention, the sequence identity is preferably 90% or higher, more preferably 95% or higher, still more preferably 98% or higher, and the most preferably 99% or higher.

Sequence identity of a base sequence is expressed as a value determined by comparing the base sequence shown under SEQ ID NO:2 in the sequence listing with a target base sequence, dividing the number of positions where bases coincide between the two base sequences by the total number of bases in the target base sequence, and further multiplying the result by 100.

Here, "a DNA including a base sequence that results from deletion, insertion, substitution and/or addition of one base or a plurality of bases in the base sequence shown under SEQ ID NO:2 in the sequence listing, and coding for a polypeptide that has activity to react with acetophenone to reduce into (S)-1-phenylethanol" may be prepared in accordance with a known method, such as described in Current Protocols in Molecular Biology (John Wiley and Sons, Inc., 1989). As long as a DNA codes for a polypeptide that has activity to react with acetophenone to reduce into (S)-1-phenylethanol, the DNA is encompassed within the above DNA.

In the base sequence shown under SEQ ID NO:2 in the sequence listing, sites where bases are to be substituted, inserted, deleted, and/or added are not particularly limited, but preferably, highly conserved regions should be avoided, and frameshift should also be avoided. Here, the term "highly conserved region" means a position where, among a plurality of enzymes derived from different sources, bases in one sequence coincide with those in other sequences when base sequences are optimally arranged in line and compared with one another. Highly conserved regions may be determined by comparing, with a tool such as GENETYX, the base sequence shown under SEQ ID NO:2 with a base sequence of an alcohol dehydrogenase that derives from a known microorganism.

A base sequence modified by substitution, insertion, deletion and/or addition may include a site modified through one type of modification process (for example, substitution), or may be include a site or sites modified through two or more modification process (for example, substitution and insertion).

The term "a plurality of bases" as mentioned above means, for example, 150 or less, preferably 100 or less, more preferably 50 or less, still more preferably 20 or less, 10 or less, 5 or less, 4 or less, 3 or less, or 2 or less bases.

Regarding Host-Vector Systems and Transformants

Insertion of a DNA that codes for the polypeptide of the present invention into an expression vector may give a polypeptide-expression vector. Then, the transformant, which is obtainable by transforming a host organism with this polypeptide-expression vector, may be cultivated to express the polypeptide of the present invention. Alternatively, a method including introducing a polynucleotide that codes for the polypeptide of the present invention into a chromosome may be utilized.

Expression vectors which may be used in the above insertion are not particularly limited as long as the vector can express a polypeptide that is encoded by the DNA. Examples of such expression vectors include plasmid vectors, phage vectors, and cosmid vectors. Shuttle vectors which can exchange a gene with another host strain may also be used.

Such a vector generally includes, for example, in the case of *Escherichia coli*, regulatory factors such as lacUV5 promoter, trp promoter, trc promoter, tac promoter, lpp promoter, tufB promoter, recA promoter, and pL promoter. The vector may be appropriately used as an expression vector that includes expression units operatably connected to the DNA of the present invention. Examples of the vector include pUCN18 (See Example 5), pSTV28 (a product of Takara Bio Inc.), and pUCNT (see WO 94/03613).

The term "regulatory factor(s)", which is used herein, means a base sequence that has a functional promoter and arbitrary related transcription elements (e.g. enhancer, CCAAT box, TATA box, and SPI site).

The term "operatably connected" as used herein means that a gene, and various regulatory elements such as promoter and enhancer, which regulate expression of a gene, are linked together each in a state operative in a host cell. It would be well known to a person skilled in the art that the type and species of the regulatory factor may vary according to the host.

Vectors, promoters, and the like, which is suitably used for each of a variety of organisms, are described in detail in, for example, "Biseibutsugaku Kisokoza 8, Idenshi-Kogaku" (Basic course of microbiology vol. 8, Gene engineering; published by Kyoritsu Shuppan Co., Ltd., Tokyo, Japan).

Host organisms which may be used for expressing polypeptides are not particularly limited provided that the organisms can be transformed by a polypeptide-expression vector that includes a DNA coding for each polypeptide, and can express a polypeptide which the introduced DNA coded for. Examples of microorganisms which may be used in the present invention include bacteria whose host-vector system has been developed, such as bacteria belonging to the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*; actinomycetes whose host-vector system has been developed, such as actinomycetes belonging to the genus *Rhodococcus* and the genus *Streptomyces*; yeasts whose host-vector system has been developed, such as yeasts belonging to the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida*; and molds whose host-vector system has been developed, such as molds belonging to the genus *Neurospora*, the genus *Aspergillus*, the genus *Cephalosporium*, and the genus *Trichoderma*. Other than microorganisms, various host-vector systems have been developed in plants or animals. In particular, systems expressing a great amount of heterogeneous proteins in insects such as silkworm (Nature, 315, 592-594 (1985)), or in plants such as coleseed, corn, and potato have been developed, and the system may be preferably utilized. Among these, bacteria are preferable in view of introduction and expression efficacy, and *Escherichia coli* is particularly preferable.

The polypeptide-expression vector including a DNA that codes for the polypeptide of the present invention may be introduced into a host microorganism by a known method. For example, explained is a case where the polypeptide-expression vector is plasmid pNCM (See Example 5), which is one of the vectors of the present invention, obtained by introducing the DNA shown under SEQ ID NO:2 into the above expression vector pUCN18, and the host microorganism is *Escherichia coli*. In this case, by introducing the polypeptide-expression vector and the host microorganism according to the protocol of commercially-available *E. coli* HB101 competent cell (a product of Takara Bio Inc.), a transformant *E. coli* HB101 (pNCM) (See Example 8) may be obtained.

A transformant may be bred, in which both of the polypeptide of the present invention and a polypeptide having ability to reproduce a reduced coenzyme, which will be mentioned below, are expressed in an identical cell. That is, the transformant may be produced by inserting a DNA that codes for the polypeptide of the present invention and a DNA that codes for a polypeptide having ability to reproduce a reduced coenzyme into one vector, and then introducing the vector into a host cell. Alternatively, such a transformant may be obtained by separately inserting these two types of DNAs into two different vectors, whose incompatible groups are different, and then introducing the vectors into one host cell. Examples of a transformant which may be produced in such a manner include *E. coli* HB101 (pNCMG) (see Example 8). *E. coli* HB101 (pNCMG) is a transformant produced by introducing a transformed vector pNCMG (see Example 6) into *E. coli* HB101 competent cell (a product of Takara Bio Inc.). The transformed vector pNCMG may be produced by introducing both the DNA shown under SEQ ID NO:2 and a DNA coding for glucose dehydrogenase, one of a polypeptide that has ability to reproduce a reduced coenzyme, into the above expression vector pUCN18. Examples of the transformant also include *E. coli* HB101 (pNCMFT) (see Example 8). *E. coli* HB101 (pNCMFT) is a transformant produced by introducing a transformed vector pNCMFT (see Examples 7) into *E. coli* HB101 competent cell (a product of Takara Bio Inc.). The transformed vector pNCMFT may be produced by inserting both the DNA shown under SEQ ID NO:2 and a DNA coding for formate dehydrogenase, one of a polypeptide that has ability to reproduce a reduced coenzyme, into the above expression vector pUCN18.

Method for Producing an Alcohol or an Aldehyde with Polypeptide or Transformant

[Reaction Condition]

A carbonyl group-containing compound may be reduced into an alcohol or an aldehyde in the following manner in the presence of the polypeptide of the present invention or a transformant in which the polypeptide of the present invention is expressed. The present invention, however, is not limited to the below methods.

A carbonyl compound substrate, such as acetophenone, is added in an appropriate solvent, such as 100 mM phosphate buffer (pH 6.5). Then, a coenzyme such as NADH and $NAD^+$, and culture of the transformant and/or a processed product of the culture are added in the phosphate buffer mixture, and the mixture is stirred to allow reaction while regulating pH of the mixture.

Here, a processed product means a processed substance having remained enzymatic catalytic activity of the polypeptide. Examples of the processed substance include a crude extract, cultivated cells, freeze-dried organisms, organisms dried over acetone, disrupted cells, or materials on which the above cells or organisms are immobilized.

The reaction may be carried out at 5° C. to 8° C., preferably 10° C. to 60° C., and more preferably 20° C. to 40° C. During the reaction, pH of the reaction mixture is 3 to 10, preferably 4 to 9, and more preferably 5 to 8. The reaction may be carried out by batch reaction or sequential reaction. For batch reaction, a reaction substrate may be added at a concentration in total volume of the loaded reaction mixture of 0.01 to 100% (w/v), preferably 0.1 to 70%, and more preferably 0.5 to 50%. For batch reaction, another portion of the reaction substrate may be further added in the course of the reaction.

For the reaction, an aqueous solvent may be used, or otherwise, a mixture of an aqueous solvent and an organic solvent may be used. Examples of the organic solvent include toluene, ethyl acetate, n-butyl acetate, hexane, isopropanol, diisopropyl ether, methanol, acetone, and dimethyl sulfoxide.

Here, a processed product of the transformant means a crude enzyme extract, cultivated cells, freeze-dried cells, organisms dried over acetone, or a disrupted product of these substances, or a mixture of them. The processed product may be used as an immobilized form of the polypeptide or cells. The immobilized form may be prepared in a known technique. In the reaction, a transformant producing both the polypeptide of the present invention and a polypeptide that has ability to reproduce a reduced coenzyme may significantly reduce a required amount of the coenzyme. Examples of such a transformant include *E. coli* HB101 (pNCMG) (See Example 8) and *E. coli* HB101 (pNCMFT) (See Example 8). Polypeptides having ability to reproduce a reduced coenzyme will be described below in detail.

[Polypeptide having Ability to Reproduce a Reduced Coenzyme]

NADH is necessary as a coenzyme in a synthesis of an alcohol compound through a reduction of a carbonyl compound with a transformant that can produce the polypeptide of the present invention. As mentioned above, the synthesis may be conducted by adding a required level of NADH in the reaction mixture. The amount of expensive coenzyme to be used may be decreased, however, by utilizing an enzyme with ability to convert an oxidized coenzyme ($NAD^+$) into reduced NADH (hereafter, the ability is referred to as "ability to reproduce a reduced coenzyme") in combination with its substrate, that is, by conducting the synthesis in the presence of a combination of coenzyme reproduction system and the polypeptide of the present invention. Examples of the enzyme with ability to reproduce the reduced coenzyme, which may be used in the above synthesis, include hydrogenases, formate dehydrogenase, alcohol dehydrogenase, glucose-6-phosphate dehydrogenase, and glucose dehydrogenase. Preferable examples include glucose dehydrogenase and formate dehydrogenase.

This reaction may be conducted by adding a coenzyme reproduction system to an asymmetric reduction reaction system. This reaction, however, may be efficiently conducted with a transformant catalyst, which is transformed by both a DNA that codes for the enzyme of the present invention and a DNA that codes for a polypeptide having ability to reproduce the reduced coenzyme, without adding another portion of an enzyme having ability to reproduce the reduced coenzyme. Such a transformant may be obtained in accordance with the method as described in the above "Regarding host-vector systems and transformants" section. Examples of such a transformant include *E. coli* HB101 (pNCMG) (See Example 8). *E. coli* HB101 (pNCMG) is a transformant produced by inserting a transformed vector pNCMG (see Example 6) into *E. coli* HB101 competent cell (a product of Takara Bio Inc.). The transformed vector pNCMG may be produced by inserting both the DNA shown under SEQ ID NO:2 and a DNA coding for glucose dehydrogenase, one of a polypeptide that has ability to reproduce a reduced coenzyme, into the above expression vector pUCN18. Examples of the transformant also include *E. coli* HB101 (pNCMFT) (see Example 8). *E. coli* HB101 (pNCMFT) is a transformant produced by inserting a transformed vector pNCMFT (see Examples 7) into *E. coli* HB101 competent cell (a product of Takara Bio Inc.). The transformed vector pNCMFT may be produced by inserting both the DNA shown under SEQ ID NO:2 and a DNA coding for formate dehydrogenase, one of a polypeptide that has ability to reproduce a reduced coenzyme, into the above expression vector pUCN18.

[Regarding a Carbonyl Group-Containing Compound, and a Product Alcohol]

A substrate carbonyl compound is not limited in a production of an alcohol or an aldehyde by reducing a carbonyl group-containing compound with the polypeptide of the present invention or a transformant in which the polypeptide of the present invention is expressed. The reaction is exceedingly valuable in the case where the carbonyl group-containing compound is an asymmetric ketone because the product of the reaction is a useful optically active alcohol.

When a carbonyl group-containing compound is 1-phenylethanone derivative, which is one of an asymmetric ketone, represented by the following formula (1):

[Chemical formula 5]

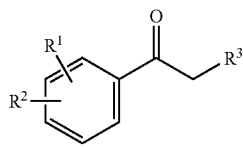

(1)

wherein $R^1$ and $R^2$ are each independently a hydrogen atom, a halogen atom, a hydroxy group, a substituted or unsubstituted alkoxy group, a substituted or unsubstituted alkyl group, an amino group or a nitro group, and $R^1$ and $R^2$ may be the same as or different from one another; $R^3$ is a hydrogen atom, a halogen atom, a hydroxy group, or a substituted or unsubstituted alkyl group;

the product is an optically active 1-phenylethanol derivative represented by the following formula (2):

[Chemical formula 6]

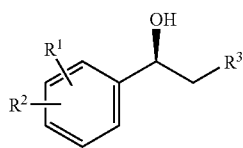

(2)

wherein $R^1$, $R^2$, and $R^3$ is the same as defined above.

When $R^1$ and $R^2$ is an substituted alkoxy or alkyl group, the substituent may be a halogen atom, a hydroxyl group, an amino group, or a nitro group.

$R^3$ is a hydrogen atom, a halogen atom, a hydroxyl group, or a substituted or unsubstituted alkyl group, and preferably a hydrogen atom.

The above "halogen atom" means a fluorine, chlorine, bromine, or iodine atom.

When a compound having a carbonyl group is an asymmetric methyl ketone compound represented by the following formula (3):

[Chemical formula 7]

(3)

wherein $R^4$ is a substituted or unsubstituted alkyl group, a substituted or unsubstituted alkenyl group, or a substituted or unsubstituted alkynyl group, the product is an optically active 1-substituted-1-ethanol derivative represented by the following formula (4):

[Chemical formula 8]

(4)

wherein $R^4$ is the same as defined above.

$R^4$ is a substituted or unsubstituted alkyl group, a substituted or unsubstituted alkenyl group, or a substituted or unsubstituted alkynyl group. $R^4$ is preferably a $C_{1-7}$ alkyl group which may be substituted by a halogen atom, a hydroxyl group, an alkoxy group, an alkoxycarbonyl group, an amino group, or a nitro group. When the substituent is an alkoxy group, a $C_{1-5}$ alkoxy group is preferable. When the substituent is an alkoxycarbonyl group, a $C_{1-5}$ alkoxycarbonyl group is preferable. Examples of such a $C_{1-5}$ alkoxycarbonyl group include methoxycarbonyl group and ethoxycarbonyl group.

Vinyl is also preferable as an example of $R^4$.

[Isolation and Purification of an Alcohol]

No particular limitation is put on a way for recovering an alcohol or aldehyde compound from a reaction mixture after the reaction. A highly-pure alcohol compound may easily be obtained by directly extracting, or extracting, after removing cells, etc., the alcohol compound from the reaction mixture with a solvent such as ethyl acetate, toluene, t-butyl methyl ether, hexane, or methylene chloride, then dehydrating the extract, and purifying the extract by distillation, recrystallization, silica gel column chromatography, or the like.

EXAMPLES

The present invention will be described below in detail with reference to Examples, but the scope of the present invention is not limited to these Examples. Detailed procedures and so on concerning the recombinant DNA technology used in the following Examples are described in the following literatures:

Molecular Cloning 2nd Edition (Cold Spring Harbor Laboratory Press, 1989), Current Protocols in Molecular Biology (Greene Publishing Associates and Wiley-Interscience).

Example 1

Purification of a Polypeptide

A polypeptide having ability to asymmetrically reduce acetophenone to produce (S)-phenylethanol was separated from *Candida maltosa* IFO 1977 strain, and purified to isolate the polypeptide in the following protocols. Purification was performed at 4° C. unless otherwise noted. Reducing activity to acetophenone was determined in accordance with the procedures described in [Method for evaluating reducing ability to a ketone or aldehyde compound].

(Cultivation of a Microorganism)

A liquid medium (400 mL, pH 7) containing 10 g/L meat extract, 10 g/L peptone, 5 g/L yeast extract, 3 g/L sodium chloride, and 0.1 g/L ADEKA NOL LG-109 (a product of ADEKA CORPORATION) was prepared in a 2-L Sakaguchi flask and steam-sterilized at 120° C. for 20 minutes. This medium was inoculated with 4 ml of culture fluid of the strain *Candida maltosa* IFO 1977, which had been prepared in advance by preculture in the same medium, and the medium was shake-cultivated at 30° C. for 60 hours.

(Preparation of a Cell-Free Extract)

Cells were collected by centrifugation from the above culture fluid, and washed with 0.8% aqueous sodium chloride.

These cells were suspended in 20 mM phosphate buffer (pH 8.0), which contained 5 mM β-mercaptoethanol, and then the cells were ultrasonically disrupted by SONIFIER 250 ultrasonic disintegrator (a product of BRANSON). The cell residues were removed from the resultant extract by centrifugation, whereby a cell-free extract was obtained.

(Thermal Treatment)

The cell-free extract obtained according to the above manner was treated at 60° C. for 30 minutes, and then centrifuged to remove insoluble matters. Thus, a thermally-treated cell-free extract was obtained.

(DEAE-Toyopearl Column Chromatography)

The cell-free extract obtained according to the above manner was applied to a DEAE-TOYOPEARL 650M column (95 ml; a product of Tosoh Corporation), which had been equilibrated in advance with 20 mM phosphate buffer (pH 6.5) that contained 5 mM β-mercaptoethanol. Unnecessary fractions were thereby adsorbed.

(Phenyl-Toyopearl Column Chromatography)

In active fractions, which were not adsorbed by the DEAE-TOYOPEARL column chromatography, ammonium sulfate was dissolved so that the final concentration of ammonium sulfate in the solution should be 0.92 M, and then precipitate was removed by centrifugation. Resultant supernatant was applied to a Phenyl-TOYOPEARL 650 M column (60 ml; a product of Tosoh Corporation), which had been equilibrated in advance with 20 mM phosphate buffer (pH 6.5) that contained 0.92 M ammonium sulfate and 5 mM β-mercaptoethanol. Active fractions were thereby adsorbed. The column was washed with 20 mM phosphate buffer (pH 6.5) that contained 0.66 M ammonium sulfate, and active fractions were eluted with a linear gradient of ammonium sulfate (from 0.66 M to 0.26 M). The active fractions were combined and dialyzed overnight with 20 mM phosphate buffer (pH 6.5) that contained 5 mM β-mercaptoethanol.

(Butyl-Toyopearl Column Chromatography)

In active fractions obtained by Phenyl-TOYOPEARL column chromatography, ammonium sulfate was dissolved so that the final concentration of ammonium sulfate in the solution should be 0.92 M. Thus-obtained solution was applied to a Butyl-TOYOPEARL 650 M column (23 ml; a product of Tosoh Corporation), which had been equilibrated in advance with 20 mM phosphate buffer (pH 6.5) that contained 0.92 M ammonium sulfate and 5 mM β-mercaptoethanol, to adsorb active fractions. The column was washed with the same buffer, and active fractions were eluted with a linear gradient of ammonium sulfate (from 0.92 M to 0 M). Electrophoretically-pure polypeptide purified sample was thereby obtained.

Hereafter, this polypeptide is referred to as "RMA".

Example 2

Physicochemical Properties of RMA

Physicochemical properties of RMA as obtained in the above manner were studied. Each activity was determined in accordance with a method as described in [Method for evaluating oxidizing ability to an alcohol compound].

[Substrate Specificity]

The activity of the RMA to oxidize (S)-2-butanol was defined as 100%. Relative activity of the RMA to each substrate was calculated as a percentage of oxidizing activity to a substrate based on the oxidizing activity to (S)-2-butanol (100%). The results are shown in Table 1. Concentration of each substrate under a condition for measuring oxidizing activity was set as illustrated in Table 1.

TABLE 1

| Substrates | mM | Relative Activity (%) |
|---|---|---|
| (S)-2-butanol | 50 | 100 |
| (R)-2-butanol | 50 | 38 |
| 2-Propanol | 100 | 66 |
| 2-Pentanol | 100 | 183 |
| 3-Pentanol | 100 | 40 |
| 2-Octanol | 5 | 134 |
| Cyclohexanol | 20 | 30 |
| (S)-1-Phenylethanol | 50 | 307 |
| (S)-1,3-Butandiol | 50 | 9.5 |
| (R)-1,3-Butandiol | 50 | 1.3 |
| 2,4-Pentandiol | 100 | 34 |
| (2R,4R)-2,4-Pentandiol | 50 | 0.5 |
| (S)-1-Amino-2-propanol | 50 | 2.0 |
| 2-Hydroxybutyric acid | 100 | 4.9 |
| Methanol | 100 | 0.6 |
| Ethanol | 100 | 5.0 |
| 1-Propanol | 100 | 4.3 |
| 1-Butanol | 100 | 6.6 |
| (S)-1,2-propandiol | 50 | 0.7 |
| (R)-1,2-Propandiol | 50 | 0.7 |

[Optimum Temperature]

Oxidizing activity to (S)-2-butanol was determined under a standard reaction condition except that the temperature was varied. The oxidizing activity at 60° C., which showed the highest activity, was defined as 100%. Relative activity of the RMA at a temperature was calculated as a percentage of oxidizing activity at the temperature based on the oxidizing activity at 60° C. (100%). The results are shown in Table 2. The temperature range that showed relative activity of not less than 60% was 45° C. to 70° C.

TABLE 2

| Temperature (° C.) | Relative Activity (%) |
|---|---|
| 25 | 17 |
| 30 | 24 |
| 37 | 39 |
| 40 | 45 |
| 45 | 68 |
| 50 | 80 |
| 55 | 88 |
| 60 | 100 |
| 65 | 91 |
| 70 | 60 |
| 75 | 29 |
| 80 | 9 |
| 85 | 0 |

[Stable Range of Temperature]

In 50 mM tris-HCl buffer (pH 8.0), RMA was treated at a temperature of 30° C. to 70° C. for 10 minutes. Then, oxidizing activity to (S)-2-butanol was measured. The oxidizing activity at 30° C. was defined as 100%, and relative activity at each temperature was calculated as a percentage of oxidizing activity at a temperature based on the oxidizing activity at 30° C. (100%). The results are shown in Table 3.

TABLE 3

| Temperature (° C.) | Relative Activity (%) |
|---|---|
| 30 | 100 |
| 35 | 96 |
| 40 | 95 |
| 50 | 75 |
| 60 | 37 |
| 70 | 9.4 |

[Optimum pH]

(S)-2-Butanol-oxidizing activity was determined with 50 mM potassium phosphate buffer (pH 7 to pH 9), 50 mM tris-HCl buffer (pH 6 to pH 8) or 50 mM glycine-sodium hydroxide buffer (pH 9 to pH 10.5) while varying pH in the reaction mixture. The highest oxidizing activity in potassium phosphate buffer at pH 9 was defined as 100%, and relative activity for each buffer and each pH was calculated as a percentage of oxidizing activity of a buffer at a certain pH based on the oxidizing activity in potassium phosphate buffer at pH 9 (100%). The results are shown in Table 4. The pH range that showed relative activity of not less than 60% was pH 7.5 to pH 9.5.

TABLE 4

| Buffer | pH | Relative activity (%) |
|---|---|---|
| Tris-HCl buffer | 7 | 47.5 |
| | 7.5 | 60.2 |
| | 8 | 84.6 |
| | 8.5 | 87.8 |
| | 9 | 100.0 |
| Potassium phosphate buffer | 6 | 41.1 |
| | 6.5 | 44.3 |
| | 7 | 52.9 |
| | 7.5 | 69.8 |
| | 8 | 76.5 |
| Glycine-sodium hydroxide buffer | 9 | 67.7 |
| | 9.5 | 61.9 |
| | 10 | 39.0 |
| | 10.5 | 34.1 |

[Stable Range of pH]

RMA was treated in 50 mM tris-HCl buffer (pH 8.0 to pH 9.0) and in 50 mM Britton-Robinson buffer (pH 5.0 to pH 12.0) at 30° C. for 30 minutes. Then, oxidizing activity to (S)-2-Butanol was determined. Activity of the untreated RMA was defined as 100%, and relative activity for a treated sample was calculated as a percentage of oxidizing activity of the treated sample based on the oxidizing activity of the untreated RMA (100%). The results are shown in Table 5. The pH range that showed relative activity of not less than 80% was pH 5.5 to pH 7.5.

TABLE 5

| Buffer | pH | Relative activity (%) |
|---|---|---|
| Britton-Robinson buffer | 4 | 21 |
| | 5 | 56 |
| | 5.5 | 81 |

TABLE 5-continued

| Buffer | pH | Relative activity (%) |
|---|---|---|
| | 6 | 87 |
| | 6.5 | 89 |
| | 7 | 83 |
| | 7.5 | 81 |
| | 8 | 42 |
| | 8.5 | 5 |
| | 9 | 1 |
| | 9.5 | 0 |
| Tris-HCl buffer | 8 | 59 |
| | 8.5 | 32 |
| | 9 | 16 |

[Inhibitor]

RMA was treated at 30° C. for 30 minutes in the presence of agents as shown in Table 6. Concentrations of agents at the time of treatment are illustrated in Table 6. Then, oxidizing activity to (S)-2-Butanol was determined in accordance with a method as described in [Method for evaluating oxidizing ability to an alcohol compound]. Activity of the untreated RMA was defined as 100%, and relative activity for each treated sample was calculated as a percentage of oxidizing activity of the treated sample based on the activity of the untreated RMA (100%) The results are shown in Table 6. Ethylenediaminetetraacetic acid, o-phenanthroline, mercury chloride, copper sulfate, or zinc sulfate inhibited RMA, whereas 2-mercaptoethanol, dithiothreitol did not.

TABLE 6

| Inhibitor | Treatment concentration of inhibitor (mM) | Relative activity (%) |
|---|---|---|
| Crotonic acid | 50 | 10.4 |
| Phenylmethanesulfonyl fluoride | 1 | 96.0 |
| N-Ethylmaleimide | 1 | 94.7 |
| Iodoacetic acid | 1 | 78.9 |
| Ethylenediaminetetraacetic acid | 1 | 12.9 |
| o-Phenanthroline | 1 | 0.0 |
| $HgCl_2$ | 1 | 0.0 |
| $CuSO_4$ | 1 | 28.5 |
| $ZnSO_4$ | 1 | 23.1 |
| Dithiothreitol | 1 | 92.2 |
| β-Mercaptoethanol | 1 | 95.4 |
| p-Hydroxybenzoic acid | 1 | 91.5 |
| p-Chloromercuribenzoate | 0.05 | 96.3 |
| $NH_2OH$ | 0.01 | 96.1 |

[Molecular Weight]

Molecular weight of RMA in reducing SDS-polyacrylamide electrophoresis was determined as approximately 39,000 based on the difference between RMA and a molecular weight standard protein in their mobility.

Example 3

Substrate Specificity of RMA in Carbonyl Reducing Activity

In 100 mM phosphate buffer (pH 6.5), which contained 0.3% (v/v) dimethyl sulfoxide, a substrate carbonyl compound and a coenzyme NADH were dissolved so that final concentration of the carbonyl compound should be 1.5 mM and that of the NADH be 0.25 mM. In the resultant solution, an appropriate amount of purified RMA, which had been prepared in Example 1, was added, and then allowed to react at 30° C. for 3 minutes. Reducing activity to each carbonyl compound was determined from reducing rate of absorbance for a reaction mixture at the wavelength of 340 nm. Reducing activity to acetophenone was defined as 100%, and determined reducing activity was converted to a relative value to reducing activity to acetophenone. The results are shown in Table 7. As is apparent from Table 7, RMA showed reducing activities to a wide variety of carbonyl compounds.,

TABLE 7

| Carbonyl compounds | Relative activity (%) |
|---|---|
| Acetone | 28 |
| 2-Butanone | 54 |
| 2-Pentanone | 141 |
| 2-Hexanone | 87 |
| 2-Heptanone | 82 |
| 2-Octanone | 95 |
| 3-Octanone | 3 |
| Chloroacetone | 92 |
| 4-Methyl-2-pentanone | 70 |
| Methyl iso-propyl ketone | 4 |
| Methyl vinyl ketone | 94 |
| Cyclopentanone | 10 |
| Acetophenone | 100 |
| o-Chloroacetophenone | 2 |
| o-Methoxyacetophenone | 10 |
| o-Hydroxyacetophenone | 9 |
| m-Chloroacetophenone | 130 |
| m-Methoxyacetophenone | 111 |
| m-Hydroxyacetophenone | 12 |
| m-Nitroacetophenone | 89 |
| p-Chloroacetohenone | 130 |
| p-Fluoroacetophenone | 110 |
| p-Methylacetophenone | 91 |
| Ethyl 4-acetylbenzoate | 70 |
| 2-Chloro-1-(3'-cholophenyl)ethanone | 20 |
| Benzylacetone | 33 |
| 2-Acetylpyridine | 63 |
| 3-Acetylpyridine | 19 |
| 4-Acetylpyridine | 83 |
| 5-Acetylfuro[2.3-c]pyridine | 63 |
| Acetypyrazine | 76 |
| 2-Acetyrfuran | 8 |
| Tetrahydrothiophen-3-one | 4 |
| 3-Chloro-2,4-pentadione | 43 |
| Acethylacetone | 19 |
| diacethyl | 24 |
| 2-Phenypropionaldehyde | 37 |
| 3-Phenypropionaldehyde | 112 |
| Propionaldehyde | 39 |
| n-Butyraldehyde | 117 |
| n-Hexylaldehyde | 117 |
| Glutaraldehyde | 9 |
| Benzaldehyde | 29 |
| m-Chlorobenzaldehyde | 87 |
| p-Chlorobenzaldehyde | 51 |
| o-Nitrobenzeldehyde | 29 |
| m-Nitrobenzaldehyde | 28 |
| p-Nitrobenzaldehyde | 27 |
| 2-Pyridinecarbaldehyde | 11 |
| 4-Pyridinecarbaldehyde | 5 |
| Methyl pyruvate | 71 |
| Ethyl pyruvate | 87 |
| Methyl 2-oxodecanate | 2 |
| Ethyl 4-chloroacetoacetate | 52 |
| Methyl 4-chloroacetoacetate | 35 |
| Ethyl 3-oxobutanoate | 93 |
| Ethyl 3-oxohexanate | 2 |
| Benzyl acetoacetate | 115 |
| n-Octyl 4-chloroacetoacetate | 24 |
| Ethyl 4-azideacetoacetate | 21 |
| Ethyl 4-benzyloxyacetoacetate | 10 |
| Ethyl 2-chloroacetoacetate | 26 |
| tert-Butylacetoacetate | 88 |
| Methyl acetoacetate | 66 |
| Acetoacetoanilide | 1 |
| o-Acetoacetanisidide | 35 |

TABLE 7-continued

| Carbonyl compounds | Relative activity (%) |
|---|---|
| N-Acetoacetyl-p-toluidine | 2 |
| 4'-Chroloacetoacetanilide | 4 |
| 2',5'-Dichloro acetoacetanilide | 34 |
| Acetoacetamide | 10 |

Example 4

Acquisition of a DNA Coding for RMA (Construction of PCR Primers)

Purified RMA, which had been obtained in Example 1, was denatured in the presence of 8 M urea, and then digested with *achromobacter*-derived lysyl endopeptidase (available from Wako Pure Chemical Industries, Ltd.). Then, the amino acid sequence of thus-obtained peptide fragment was determined by ABI492-type protein sequencer (a product of Perki-nElmer). Based on a DNA sequence which was expected from the amino acid sequence, primer 1: 5'-GGTGATTGGT-TYGGTTTRGG-3' (SEQ ID NO:3 in the sequence listing), and primer 2: 5'-SWAGCACCYAAACCAACTGG-3' (SEQ ID NO:4 in sequence listing), which were for amplifying a part of a gene that codes for RMA in PCR, were synthesized.

(Amplification of a Gene Through PCR)

Chromosomal DNA was extracted from cells of *Candida maltosa* IFO 1977 strain, which had been cultivated in a similar manner to Example 1, with GENtorukun™ (a product of Takara Bio Inc.) in accordance with the condition illustrated in an instruction manual. Then, PCR was carried out with the DNA primers 1 and 2, which had been prepared in the above manner, in the presence of the obtained chromosomal DNA as a template. As a result, an about 0.5 kbp DNA fragment assumed to be a part of a target gene was amplified. PCR was carried out with TaKaRa Ex Taq (a product of Takara Bio Inc.) as a DNA polymerase under a reaction condition as illustrated in an instruction manual. This DNA fragment was subjected to direct sequencing with BigDye Terminator Cycle Sequencing Kit (a product of Applied Biosystems) and Applied Biosystems 3130xl Genetic Analyzer (a product of Applied Biosystems), and thereby the base sequence of the DNA fragment was analyzed. The base sequence acquired is illustrated as SEQ ID NO:5 in the sequence listing.

(Determination of Complete Sequence of a Target Gene by Inverse PCR Method)

Chromosomal DNA of *Candida maltosa* IFO 1977 strain, which had been prepared in the above manner, was completely digested with a restriction enzyme BglI or MunI or XbaI, and then the thus-obtained mixture of DNA fragments was intramolecularly-cyclized with T4 ligase. With the cyclized product as a template, the complete base sequence of RMA gene, which included the above base sequence shown under SEQ ID NO:5 in the sequence listing, was determined by inverse PCR method (Nucl. Acids Res., 16, 8186 (1988)). The result is shown under SEQ ID NO:2 in the sequence listing. Inverse PCR was carried out with Pyrobest DNA Polymerase (a product of Takara Bio Inc.) as a DNA polymerase, and the reaction condition was followed by the condition illustrated in an instruction manual. In addition, an amino acid sequence coded by the base sequence shown under SEQ ID NO:2 was illustrated in SEQ ID NO:1.

Example 5

Construction of a Recombinant Vector pNCM

PCR was carried out with primer 3: 5'-GGGAATTC-CATATGTCAATTCCATCTACTCAATAC-3' (SEQ ID NO:6 in the sequence listing), primer 4: 5'-CCGGAATTCT-TATGGATGGAAAACAACTCTACC-3'(SEQ ID NO:7 in the sequence listing) in the presence of the chromosomal DNA of *Candida maltosa* IFO 1977 strain as a template. As a result, a double-stranded DNA was obtained, in which an NdeI recognition site was inserted in a initiation codon position, and an EcoRI recognition site was inserted at a position immediately downstream of the termination codon, in the gene that consisted of the base sequence shown under SEQ ID NO:2 in the sequence listing. PCR was carried out with Pyrobest DNA Polymerase (a product of Takara Bio Inc.) as DNA polymerase, and the reaction condition was followed by the condition illustrated in an instruction manual.

A DNA fragment obtained by the above PCR was digested with NdeI and EcoRI, and then inserted at the site between the NdeI recognition site and the EcoRI recognition site, downstream of the lac promoter of the plasmid pUCN18 (a plasmid constructed by replacing "T" at the 185th position with "A" of pUC18 (a product of Takara Bio Inc., GenBank Accession No. L09136) by PCR to destroy the NdeI site, and further replacing "GC" at the 471st and 472nd positions with "TG" to introduce a new NdeI site) Thus, a recombinant vector pNCM was constructed. The method for constructing pNCM and the structure thereof are illustrated in FIG. 1.

Example 6

Construction of a Recombinant Vector pNCMG that Further contains a Glucose Dehydrogenase Gene PCR was carried out with primer 5: 5'-CCGGAAT-TCTAAGGAGGTTAACAATGTATAAAG-3'(SEQ ID NO:8 in the sequence listing) and primer 6: 5'-ACGCGTCGACT-TATCCGCGTCCTGCTTGG-3' (SEQ ID NO:9 in the sequence listing) in the presence of the plasmid pGDK1 (a person skilled in the art could acquire or prepare the plasmid in accordance with the way as described in Eur. J. Biochem., 186, 389 (1989)) as a template. As a result, a double-stranded DNA was obtained, in which a ribosome binding site of *Escherichia coli* was inserted at a position 5-base upstream from the initiation codon of a glucose dehydrogenase (hereafter to be abbreviated as "GDH") gene that was derived from *Bacillus megaterium* IAM 1030 strain, and an EcoRI recognition site was inserted immediately upstream of the ribosome binding site, and further, SalI recognition site was inserted immediately downstream of the termination codon.

Thus-obtained DNA fragment was digested with EcoRI and SalI, and then inserted at the site between the EcoRI recognition site and the SalI recognition site, downstream of the RMA gene of the plasmid pNCM as described in Example 5 to construct a recombinant vector pNCMG. The method for constructing pNCMG and the structure thereof are illustrated in FIG. 1.

Example 7

Construction of a Recombinant Vector pNCMFT that Further contains Formate Dehydrogenase Gene PCR was carried out with primer 7: 5'-ACCACCGAAT-TCTAAGGAGGTTAACAATGGCGAAA-3' (SEQ ID NO:10 in the sequence listing), primer 8: 5'-CCACCA-GAGCTCTCAGCCGGCCTTCTTGAAC-3' (SEQ ID NO:11 in the sequence listing), primer 9: 5'-TCGGCGTC-GACGAGTTCCTTCTCGAACAC-3' (SEQ ID NO:12 in the sequence listing), primer 10: 5'-GTGTTCGAGAAG-GAACTCGTCGACGCCGA-3' (SEQ ID NO:13 in the sequence listing) in the presence of the plasmid pFT002 (a person skilled in the art could acquire or prepare the plasmid in accordance with the way as described in WO 2003/031626) as a template. An about 0.3 kbp double-stranded DNA was produced by combining the primers 7 and 9, and an about 0.9 kbp double-stranded DNA was produced by combining the primers 8 and 10. Then, a combination of primers 7 and 8 was subjected to PCR with a mixture of these double-stranded DNAs as templates. As a result, a double-stranded DNA was obtained, in which a ribosome binding site of *Escherichia coli* was inserted at a position 5-base upstream from the initiation codon of a formate dehydrogenase (hereafter to be abbreviated as "FDH") gene of *Thiobacillus* sp., which had been constructed by replacing "G" at the 354th position of the base sequence that is shown under SEQ ID NO:3 in sequence listing of WO 2003/031626 with "A", and an EcoRI recognition site was inserted immediately upstream of the ribosome binding site, and further an SacI recognition site was added immediately downstream of the termination codon. Thus-obtained DNA fragment was digested with EcoRI and SacI, and then inserted at the site between the EcoRI recognition site and the SalI recognition site, downstream of the RMA gene of the plasmid pNCM as described in Example 5 to construct a recombinant vector pNCMFT. The method for constructing pNCMFT and the structure thereof are illustrated in FIG. 1.

Example 8

Construction of a Transformant

*E. coli* HB101 (pNCM) was produced by transforming *E. coli* HB101 competent cell (a product of Takara Bio Inc.) with the recombinant vector pNCM, which had been constructed in Example 5.

*E. coli* HB101 (pNCMG) was produced by transforming *E. coli* HB101 competent cell (a product of Takara Bio Inc.) with the recombinant vector pNCMG, which had been constructed in Example 6.

*E. coli* HB101 (pNCMFT) was produced by transforming *E. coli* HB101 competent cell (a product of Takara Bio Inc.) with the recombinant vector pNCMFT, which had been constructed in Example 7.

Example 9

Expression of DNA in a Transformant

Three transformants obtained in Example 8, and *E. coli* HB101 (pUCN18) (Comparative example), which is a transformant containing a vector plasmid pUCN18, were each inoculated into a 5 ml of 2×YT medium (tryptone 1.6%, yeast extract 1.0%, NaCl 0.55%, and pH 7.0), which contained 200 µg/ml of ampicillin, and then shake-cultivated at 37° C. for 24 hours. Cells were collected by centrifugation, and suspended in 5 ml of 100 mM phosphate buffer (pH 6.5). Cells in the obtained suspension were disrupted with UH-50 ultrasonic homogenizer (a product of SMT Co., Ltd), and then cell residue was removed by centrifugation, to give a cell-free extract. The acetophenone-reducing activity by RMA, GDH activity, and FDH activity were tested on this cell-free extract.

Reducing activity to acetophenone was determined in accordance with a manner as described in the above [Method for evaluating reducing ability to a ketone or aldehyde compound]. The GDH activity was determined by, first, adding 0.1 M glucose, 2 mM coenzyme NAD, and crude enzyme liquid in 1 M tris-HCl buffer (pH 8.0), then allowing the mixture to react at 25° C. for 1 minute and calculating the GDH activity from increasing rate of absorbance for the reaction mixture at the wavelength of 340 nm. The FDH activity was determined by, first, adding 0.5 M formic acid, 2 mM coenzyme NAD, and crude enzyme liquid in 100 mM phosphate buffer (pH 7.0), then allowing the mixture to react at 30° C. for 1 minute and calculating the FDH activity from increasing rate of absorbance for the reaction mixture at the wavelength of 340 nm. Under these reaction conditions, enzyme activity 1 U was defined as enzyme activity that reduced 1 μm of NAD to NADH per minute.

RMA, GDH and FDH were summarized in Table 8 as specific activities. As illustrated in Table 8, acetophenone-reducing activity and RMA expression were observed for three transformants as obtained in Example 8. Also, GDH expression 20 was observed for *E. coli* HB101 (pNCMG), which contained the GDH gene, and FDH expression was observed for *E. coli* HB101 (pNCMFT), which contained the FDH gene.

TABLE 8

| Strain | RMA specific activity (U/mg) | GDH specific activity (U/mg) | FDH specific activity (U/mg) |
|---|---|---|---|
| *E. coli* HB101 | 0 | 0 | 0 |
| *E. coli* HB101 (pUCN18) | 0 | 0 | 0 |
| *E. coli* HB101 (pNCM) | 21.6 | 0 | 0 |
| *E. coli* HB101 (pNCMG) | 17.7 | 42.5 | 0 |
| *E. coli* HB101 (pNCMFT) | 14.7 | 0 | 3.4 |

Example 10

Production of (S)-phenylethanol with Transformant *E. coli* HB101 (pNCM)

*E. coli* HB101 (pNCM) was cultivated in a similar manner to Example 9, and then cells were disrupted with an ultrasonic homogenizer. Thus, 100 mL of the cell-free extract was produced. In a 100-mL portion of this cell-free extract, 700 U of a glucose dehydrogenase (Trade name: GLUCDH "Amano" II, a product of Amano Enzyme Inc.), 17 g of glucose, 3 mg of NAD$^+$, and 10 g of acetophenone were added, and the mixture was stirred at 30° C. for 20 hours while controlling the pH of the reaction mixture to 6.5 with 5 N aqueous sodium hydroxide, which was added dropwise to the mixture. After the reaction, the reaction mixture was extracted with toluene, and combined organic layer was dried over anhydrous sodium sulfate. Removal of sodium sulfate, and evaporation of organic solvents from the organic layer yielded 9.8 g of (S)-phenylethanol. The product (S)-phenylethanol was analyzed in accordance with the [Analysis condition (1) for gas chromatography] as described above, and found that the optical purity of the product was 99.9% e.e. or higher.

Example 11

Production of (S)-phenylethanol with Transformant *E. coli* HB101 (pNCMG)

Culture fluid was obtained by cultivating *E. coli* HB101 (pNCMG) in a similar manner to Example 9. In a 100-mL portion of the culture fluid, 17 g of glucose, 3 mg of NAD$^+$, and 10 g of acetophenone were added and the mixture was stirred at 30° C. for 20 hours while controlling the pH of the reaction mixture to 6.5 with 5 N aqueous sodium hydroxide, which was added dropwise to the mixture. After the reaction, the reaction mixture was extracted with toluene, and combined organic layer was dried over anhydrous sodium sulfate. Removal of sodium sulfate, and evaporation of organic solvents from the organic layer under reduced pressure yielded 9.9 g of (S)-phenylethanol. The product (S)-phenylethanol was analyzed in accordance with the [Analysis condition (1) for gas chromatography] as described above, and found that the optical purity of the product was 99.9% e.e. or higher.

Example 12

Production of (S)-phenylethanol with Transformant *E. coli* HB101 (pNCMFT)

Culture fluid was obtained by cultivating *E. coli* HB101 (pNCMFT) in a similar manner to Example 9. In a 100-mL portion of the culture fluid, 2.8 g of sodium formate, 3 mg of NAD$^+$, and 10 g of acetophenone were added, and the mixture was stirred at 30° C. for 20 hours while controlling the pH of the reaction mixture to 6.0 with 5 N aqueous formic acid, which was added dropwise to the mixture. After the reaction, the reaction mixture was extracted with toluene, and combined organic layer was dried over anhydrous sodium sulfate. Removal of sodium sulfate, and evaporation of organic solvents from the organic layer under reduced pressure yielded 9.8 g of (S)-phenylethanol. The product (S)-phenylethanol was analyzed in accordance with the [Analysis condition (1) for gas chromatography] as described above, and found that the optical purity of the product was 99.9% e.e. or higher.

Example 13

Production of (S)-3-buten-2-ol with Transformant *E. coli* HB101 (pNCM)

*E. coli* HB101 (pNCM) was cultivated in a similar manner to Example 9, and then cells were disrupted with an ultrasonic homogenizer. Thus, 100 mL of the cell-free extract was produced. In a 100-mL portion of this cell-free extract, 2000 U of a glucose dehydrogenase (Trade name: GLUCDH "Amano" II, a product of Amano Enzyme Inc.), 18.4 g of glucose, and 10 mg of NAD$^+$ were added, and the mixture was stirred at 30° C. In the mixture, 1.05 g of methyl vinyl ketone was added and continued stirring at 30° C. while controlling the pH of the reaction mixture to 5.5 with 5 N aqueous sodium hydroxide, which was added dropwise to the mixture. Five more portions of 1.05 g of methyl vinyl ketone were added every 15 minutes (total added amount of methyl vinyl ketone was 6.3 g). After 19-hour reaction, the reaction mixture was repeatedly extracted with 200 ml of methylene chloride five times, and obtained organic layers were combined, followed by drying over anhydrous sodium sulfate. Sodium sulfate was removed by filtration and organic solvents were eliminated by evaporation under an ordinary pressure. The residue was distilled under an ordinary pressure to yield 4.5 g of (S)-3-buten-2-ol (Boiling point: 96° C.). The optical purity of the product was 99.6% e.e. Yield of (S)-3-buten-2-ol was determined from an analysis under the below condition for gas chromatography.

[Analysis Condition for Gas Chromatography]
Column: InertCap5 (30 m×0.25 mm; a product of GL Sciences Inc.)
Detector: FID
Carrier gas: Helium
Column temperature: 35° C.

Optical purity of the produced 3-buten-2-ol was determined by first converting the 3-buten-2-ol into a corresponding dinitrobenzoyl compound, and then analyzing the compound by HPLC. Conversion of 3-buten-2-ol into the corresponding dinitrobenzoyl compound was carried out as follows. 3-Buten-2-ol was extracted from the reaction mixture with methylene chloride, then triethylamine and 3,5-dinitrbenzoyl chloride (1.2 equivalents to 3-buten-2-ol) were added to extracted 3-buten-2-ol, and the mixture was stirred at a room temperature for 2 hours. The reaction mixture was washed with 1 N aqueous HCl, and then purified by preparative thin-layer chromatography. Thus-obtained fraction was dissolved in ethanol, and then analyzed under the condition for high performance liquid chromatography as listed below.

[Analysis Condition of High Performance Liquid Chromatography]
Column: Chiralpak AD-H (250 mm×4.6 mm, a product of Daicel Chemical Industries)
Eluent: n-hexane/ethanol=7/3
Flow rate: 1.0 ml/min
Detection: 245 nm
Elution time: S form: 17.2 minutes, R form: 11.0 minutes Example 14

Production of (S)-3-buten-2-ol with Transformant *E. coli* HB101 (pNCMG)

Culture fluid was obtained by cultivating *E. coli* HB101 (pNCMG) in a similar manner to Example 9. In a 100-mL portion of the culture fluid, 7.1 g of glucose, 10 mg of $NAD^+$, and 5 g of EMULGEN 810 (a product of Kao Corporation) were added, and the mixture was stirred at 30° C. for 10 minutes. In this mixture, 2.63 g of methyl vinyl ketone was added, and the mixture was continued stirring at 30° C. while controlling the pH of the reaction mixture to 5.5 with 5 N aqueous sodium hydroxide, which was added dropwise to the mixture. After 3-hour reaction, the reaction mixture was repeatedly extracted with 200 ml of methylene chloride five times, and obtained organic layers were combined, followed by drying over anhydrous sodium sulfate. Sodium sulfate was removed by filtration and organic solvents were eliminated by evaporation under an ordinary pressure. The residue was distilled under an ordinary pressure to yield 2.54 g of (S)-3-buten-2-ol. The optical purity of the product was 99.2% e.e. Yield and optical purity of (S)-3-buten-2-ol were determined in accordance with the manner as described in Example 13.

Example 15

Production of (S)-3-buten-2-ol with Transformant *E. coli* HB101 (pNCMFT)

Culture fluid was obtained by cultivating *E. coli* HB101 (pNCMFT) in a similar manner to Example 9. In a 100-mL portion of the culture fluid, 1.94 g of sodium formate, and 10 mg of $NAD^+$ were added, and the mixture was stirred at 30° C. In this mixture, 0.525 g of methyl vinyl ketone was added, and the mixture was continued stirring at 30° C. while controlling the pH of the reaction mixture to 5.5 with 5 N aqueous formic acid, which was added dropwise to the mixture. Seven more portions of 0.525 g of methyl vinyl ketone were added every 30 minutes (total added amount of methyl vinyl ketone was 4.2 g). After 19-hour reaction, the reaction mixture was extracted repeatedly with 200 ml of methylene chloride five times, and obtained organic layers were combined, followed by drying over anhydrous sodium sulfate. Sodium sulfate was removed by filtration and organic solvents were eliminated by evaporation under an ordinary pressure. The residue was distilled under an ordinary pressure to yield 3.94 g of (S)-3-buten-2-ol. The optical purity of the product was 96.33% e.e. Yield and optical purity of (S)-3-buten-2-ol were determined in accordance with the manner as described in Example 13.

Example 16

Production of (S)-2-hydroxy-5-pentanol with Transformant *E. coli* HB101 (pNCMG)

Culture fluid was obtained by cultivating *E. coli* HB101 (pNCMG) in a similar manner to Example 9. In a 50-mL portion of the culture fluid, 21.2 g of glucose, 2.5 mg of $NAD^+$, and 10.0 g of 2-oxo-5-pentanol were added, and the mixture was continued stirring at 30° C. while controlling the pH of the reaction mixture to 6.5 with 5 N aqueous sodium hydroxide, which was added dropwise to the mixture. After 45-hour reaction, cells were removed from the reaction mixture by centrifugation. The resultant solution was repeatedly extracted with 200 ml of ethyl acetate 3 times, and obtained organic layers were combined, followed by drying over anhydrous sodium sulfate. Sodium sulfate was removed by filtration and organic solvents were eliminated by evaporation under an ordinary pressure. Then, solvents were evaporated, to yield 8.68 g of (S)-2-hydroxy-5-pentanol. Optical purity of the produced (S)-2-hydroxy-5-pentanol was 99.2% e.e. Yield of (S)-2-hydroxy-5-pentanol was determined under the following condition (a) for gas chromatography, and optical purity thereof was determined under the following condition (b) for gas chromatography.

[Analysis Condition (a) for Gas Chromatography]
Column: InertCap5 (30 m×0.25 mm; a product of GL Sciences Inc.)
Detector: FID
Carrier gas: Helium
Column temperature: 80° C.

[Analysis Condition (b) for Gas Chromatography]
Column: InertCap CHIRAMIX (30 m×0.25 mm; a product of GL Sciences Inc.)
Detector: FID
Carrier gas: Helium
Column temperature: 90° C.
Elution time: S-form: 17.2 minutes, R-form: 18.3 minutes Example 17

Production of methyl(S)-3-hydroxybutyrate with Transformant *E. coli* HB101 (pNCMFT)

Culture fluid was obtained by cultivating *E. coli* HB101 (pNCMFT) in a similar manner to Example 9. In a 100-mL portion of the culture fluid, 2.8 g of sodium formate, 3 mg of $NAD^+$, and 10 g of methyl acetoacetate were added, and the mixture was stirred at 30° C. for 20 hours while controlling the pH of the reaction mixture to 6.0 with 5 N aqueous formic acid, which was added dropwise to the mixture. After the reaction, the reaction mixture was extracted with toluene, and combined organic layer was dried over anhydrous sodium sulfate. Removal of sodium sulfate, and evaporation of organic solvents from the organic layer under reduced pressure yielded 9.7 g of methyl (S)-3-hydroxybutyrate. The optical purity of the product was 99% e.e. or higher. Yield of ethyl(S)-3-hydroxybutyrate was calculated based on the analysis under the following condition for gas chromatography.

[Analysis Condition of Gas Chromatography]
Column: TC-WAX (15 m×0.25 mm; a product of GL Sciences Inc.)
Detector: FID
Column temperature: 85° C.
Injector temperature: 200° C.
Detector temperature: 200° C.
Carrier gas: Helium (70 kPa)
Split ratio: 100/1
Elution time: methyl acetoacetate: 2.9 minutes, methyl 3-hydroxybutyrate: 3.8 minutes Optical purity of the produced methyl (S)-3-hydroxybutyrate was determined by first converting the methyl(S)-3-hydroxybutyrate into a corresponding dinitrobenzoyl compound, and then analyzing the compound in accordance with the following condition for high performance liquid chromatography. Conversion of methyl 3-hydroxybutanoate into the corresponding dinitrobenzoyl compound was carried out as follows. Methyl 3-hydroxybutanoate was extracted from the reaction mixture with ethyl acetate, then pyridine and 3,5-dinitrobenzoyl chloride (1.2 equivalents to methyl 3-hydroxybutanoate) was added to extracted methyl 3-hydroxybutanoate, and the mixture was stirred at a room temperature for 2 hours. The reaction mixture was washed with 1 N aqueous HCl, and then purified by preparative thin-layer chromatography. Thus-obtained fraction was dissolved in ethanol, and then analyzed under the following HPLC condition.

[Analysis Condition for High Performance Liquid Chromatography]
Column: Chiralpak AD-H (a product of Daicel Chemical Industries, Ltd.)
Detection wavelength: 230 nm
Column temperature: 20° C.
Eluent: n-hexane/ethanol=3/7
Flow rate: 0.7 ml/min
Elution time: (S)-form: 21.7 minutes, (R)-form: 29.8 minutes

The invention claimed is:

1. A purified DNA which is any one of the following DNAs (A), (B), (C), and (D):
   (A) a DNA comprising the nucleotide sequence shown under SEQ ID NO:2 in the sequence listing;
   (B) a DNA hybridizable under a stringent condition with a DNA that comprises the nucleotide sequence complementary to the nucleotide sequence shown under SEQ ID NO:2 in the sequence listing, and coding for a polypeptide that has activity to react with acetophenone to reduce into (S)-1-phenylethanol, wherein said DNA hybridizable under a stringent condition is obtainable by hybridization with a filter in the presence of 0.7 to 1.0 M NaCl, at 65° C., followed by washing the filter with a 0.2-fold concentration of SSC solution at 65° C.;
   (C) a DNA having sequence identity of 90% or higher to the nucleotide sequence shown under SEQ ID NO:2 in the sequence listing, and coding for a polypeptide that has activity to react with acetophenone to reduce into (S)-1-phenylethanol; and
   (D) a DNA comprising a nucleotide sequence that results from deletion, insertion, substitution and/or addition of 100 or less nucleotides in the nucleotide sequence shown under SEQ ID NO:2 in the sequence listing, and coding for a polypeptide that has activity to react with acetophenone to reduce into (S)-1-phenylethanol.

2. A purified DNA coding for a polypeptide which is derived from *Candida maltosa* and has the following physicochemical properties (1) to (6):

(1) Action:
   The polypeptide oxidizes an alcohol with NAD$^+$ as a coenzyme to produce a ketone or an aldehyde, or reduces a ketone or an aldehyde with NADH as coenzyme to produce an alcohol;

(2) Substrate specificity:
   A substrate in oxidation reaction is an aliphatic alcohol which may have an aromatic substituent, and the polypeptide preferentially oxidizes (S)-2-butanol in comparison with (R)-2-butanol; and a substrate in reduction reaction is a ketone or an aldehyde, and the polypeptide reacts with acetophenone to reduce into (S)-1-phenylethanol;

(3) Molecular weight:
The molecular weight of the polypeptide is approximately 39,000 as determined by reducing SDS-polyacrylamide gel electrophoresis;

(4) Stability in pH:
Stable pH range of the polypeptide is 5.5 to 7.5;

(5) Optimum temperature:
Optimum temperature of the polypeptide for action is 45° C. to 70° C.;

(6) Inhibitor:
Enzyme activity of the polypeptide is inhibited by ethylenediaminetetraacetic acid, o-phenanthroline, mercury chloride, copper sulfate or zinc sulfate, whereas is not inhibited by 2-mercaptoethanol or dithiothreitol.

3. A vector comprising the DNA according to claim 1.
4. The vector according to claim 3,
wherein the polypeptide with ability to reproduce a reduced coenzyme is glucose dehydrogenase or formate dehydrogenase.
5. A transformant
which is producible by transformation of a host cell with the vector according to claim 3.
6. The transformant according to claim 5,
wherein the host cell is *Escherichia coli*.
7. A method for producing an alcohol comprising
reacting the transformant according to claim 5 or 6, and/or a processed product of the transformant with a carbonyl group-containing compound.
8. The method for producing an alcohol according to claim 7,
wherein the carbonyl group-containing compound is an asymmetric ketone, and a product therefrom is an optically active alcohol.
9. The method for producing an alcohol according to claim 8, wherein the asymmetric ketone is a 1-phenylethanone derivative represented by the following formula (1):

[Chemical formula 1]

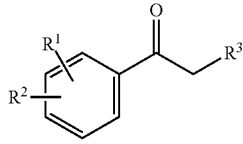

(1)

wherein $R^1$ and $R^2$ are each independently a hydrogen atom, a halogen atom, a hydroxy group, a substituted or unsubstituted alkoxy group, a substituted or unsubstituted alkyl group, an amino group or a nitro group, and $R^1$ and $R^2$ may be the same as or different from one another; $R^3$ is a hydrogen atom, a halogen atom, a hydroxy group or a substituted or unsubstituted alkyl group; and the product optically active alcohol therefrom is an optically active 1-phenylethanol derivative represented by the following formula (2):

[Chemical formula 2]

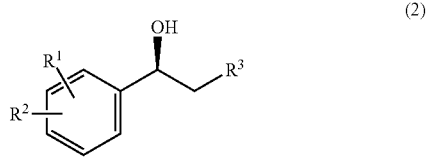

(2)

wherein $R^1$, $R^2$ and $R^3$ are the same as defined above.

10. The method for producing an alcohol according to claim 9,
wherein $R^3$ is a hydrogen atom.
11. The method for producing an alcohol according to claim 8,
wherein the asymmetric ketone is a methyl ketone compound represented by the following formula (3):

[Chemical formula 3]

(3)

wherein $R^4$ is a substituted or unsubstituted alkyl group, a substituted or unsubstituted alkenyl group or a substituted or unsubstituted alkynyl group, and
the product optically active alcohol therefrom is an optically active 1-substituted-1-ethanol derivative represented by the formula (4):

[Chemical formula 4]

(4)

wherein $R^4$ is the same as defined above.

12. The method for producing an alcohol according to claim 11,
wherein $R^4$ is a $C_{1-7}$ alkyl group which may be substituted by a halogen atom, a hydroxy group, an alkoxy group, an alkoxycarbonyl group, an amino group or a nitro group.

13. The method for producing an alcohol according to claim 11,
wherein $R^4$ is a vinyl group.

* * * * *